United States Patent
Yamamoto et al.

(10) Patent No.: US 11,382,911 B2
(45) Date of Patent: Jul. 12, 2022

(54) PLANT EXTRACT CONTAINING DIKETOPIPERAZINE AND METHOD FOR PRODUCING SAME

(71) Applicant: SUNTORY HOLDINGS LIMITED, Osaka (JP)

(72) Inventors: Kenji Yamamoto, Kanagawa (JP); Yoshinori Beppu, Osaka (JP); Koichi Nakahara, Osaka (JP); Tomonori Suzuki, Kanagawa (JP); Soichiro Shima, Tokyo (JP); Yuka Murakami, Osaka (JP)

(73) Assignee: SUNTORY HOLDINGS LIMITED, Osaka (JP)

(*) Notice: Subject to any disclaimer, the term of this patent is extended or adjusted under 35 U.S.C. 154(b) by 50 days.

(21) Appl. No.: 16/516,622

(22) Filed: Jul. 19, 2019

(65) Prior Publication Data

US 2019/0336569 A1 Nov. 7, 2019

Related U.S. Application Data

(62) Division of application No. 14/896,953, filed as application No. PCT/JP2014/065388 on Jun. 10, 2014, now abandoned.

(51) Int. Cl.

| | |
|---|---|
| A61K 36/185 | (2006.01) |
| A61K 36/48 | (2006.01) |
| A61K 36/899 | (2006.01) |
| A61K 36/00 | (2006.01) |
| A61K 31/495 | (2006.01) |
| A23F 3/16 | (2006.01) |
| A23L 33/105 | (2016.01) |
| A23L 33/17 | (2016.01) |
| A23L 33/18 | (2016.01) |
| C07D 241/08 | (2006.01) |
| A61K 36/82 | (2006.01) |
| A61K 38/12 | (2006.01) |

(52) U.S. Cl.
CPC ............ *A61K 31/495* (2013.01); *A23F 3/16* (2013.01); *A23F 3/166* (2013.01); *A23L 33/105* (2016.08); *A23L 33/17* (2016.08); *A23L 33/18* (2016.08); *A61K 36/185* (2013.01); *A61K 36/48* (2013.01); *A61K 36/82* (2013.01); *A61K 36/899* (2013.01); *A61K 38/12* (2013.01); *C07D 241/08* (2013.01); *A23V 2002/00* (2013.01); *A61K 2236/19* (2013.01); *A61K 2236/37* (2013.01)

(58) Field of Classification Search
None
See application file for complete search history.

(56) References Cited

U.S. PATENT DOCUMENTS

| | | |
|---|---|---|
| 5,034,609 A | 7/1991 | Satake et al. |
| 2003/0060428 A1 | 3/2003 | Hermansen et al. |
| 2007/0116840 A1 | 5/2007 | Prakash et al. |
| 2007/0286938 A1 | 12/2007 | Saiki et al. |
| 2008/0107787 A1 | 5/2008 | Prakash et al. |
| 2012/0283178 A1 | 11/2012 | Tsuruoka et al. |
| 2014/0243514 A1 | 8/2014 | Brower III et al. |
| 2016/0106130 A1 | 4/2016 | Yamamoto et al. |
| 2017/0129919 A1 | 5/2017 | Suzuki et al. |

FOREIGN PATENT DOCUMENTS

| | | |
|---|---|---|
| AU | 2014386720 A1 | 1/2016 |
| CN | 101461441 A | 6/2009 |
| CN | 103974628 A | 8/2014 |
| CN | 104817615 A | 8/2015 |
| EA | 201390347 A1 | 7/2013 |
| EP | 1698703 A1 | 9/2006 |
| EP | 2676556 A1 | 12/2013 |
| EP | 3158996 A1 | 4/2017 |
| EP | 3158997 A1 | 4/2017 |
| JP | 2003-521528 A | 7/2003 |
| JP | 2003-252896 A | 9/2003 |
| JP | 2005-206528 A | 8/2005 |
| JP | 2009-517038 A | 4/2009 |
| JP | 2010-166911 A | 8/2010 |
| JP | 2011-136916 A | 7/2011 |
| JP | 2012-517214 A | 8/2012 |
| JP | 2012-517998 A | 8/2012 |
| JP | 5456876 B1 | 4/2014 |
| JP | 2014-139224 A | 7/2014 |

(Continued)

OTHER PUBLICATIONS

Koichi et al. (JP-2003-252896 A (President of Toyohashi University of Technology) Sep. 10, 2003, entire text, see abstract within IDS) (Year: 2003).*
Prasad et al. (Could dietary proteins serve as cyclo (His-Pro) precursors?, Neuropeptides, May 1991, vol. 19, No. 1, pp. 17-21 within IDS) (Year: 1991).*
Ripken, Dina et al., "Steviol Glycoside Rebaudioside A Induces Glucagon-like Peptide-1 and Peptide YY Release in a Porcine ex Vivo Intestinal Model", Journal of Agricultural and Food Chemistry, 2014, 62, pp. 8365-8370; Cited in CN Office Action dated Aug. 28, 2020.

(Continued)

*Primary Examiner* — Michael Barker
*Assistant Examiner* — Randall O Winston
(74) *Attorney, Agent, or Firm* — WHDA, LLP

(57) ABSTRACT

A diketopiperazine mixture suitable for mixing with a food or drink and a method for producing the mixture. High-temperature and high-pressure treatment of plant peptides in a liquid allows production of a plant extract containing a high concentration of diketopiperazines including cyclo-leucyl-leucine and cyclo-leucyl-phenylalanine. Diketopiperazines having excellent flavor derived from a plant natural product and can produce a food or drink provided with the functions of the diketopiperazines by directly mixing the diketopiperazines with the food or drink.

8 Claims, 2 Drawing Sheets

(56) References Cited

FOREIGN PATENT DOCUMENTS

| JP | 5690028 B1 | 3/2015 |
|---|---|---|
| WO | 2006/116814 A1 | 11/2006 |
| WO | 2011-077759 A1 | 6/2011 |
| WO | 2011-077761 A1 | 6/2011 |
| WO | 2012/033789 A2 | 3/2012 |
| WO | 2012/111820 A1 | 8/2012 |
| WO | 2013/176738 A1 | 11/2013 |
| WO | 2014/200000 A1 | 12/2014 |
| WO | 2015/194070 A1 | 12/2015 |
| WO | 2015/194205 A1 | 12/2015 |
| WO | 2015/194447 A1 | 12/2015 |

OTHER PUBLICATIONS

Temizkan, S. et al., "Sucralose enhances GLP-1 release and lowers blood glucose in the presence of carbohydrate in healthy subjects but not in patients with type 2 diabetes", European Journal of Clinical Nutrition, 2015, 69, pp. 162-166; Cited in CN Office Action dated Aug. 28, 2020.

Giessen et al. "Rational and combinatorial tailoring of bioactive cyclic dipeptides," Frontiers in Microbiology, 2015, vol. 6, Article 785 , pp. 1-11 (Year: 2015); Cited in Non-Final Office Action dated Oct. 8, 2020.

Ortiz et al. "Cyclic Di peptides: Secondary Metabolites Isolated from Different Microorganisms with Diverse Biological Activities," Current Medicinal Chemistry, 2017, 24, 2773-2780 (Year: 2017) ; Cited in Non-Final Office Action dated Oct. 8, 2020.

Medline Plus entry for Blood sugar (downloaded from medlineplus. gov/bloodsugar.html on Oct. 1, 2020) (Year 2020); Cited in Non-Final Office Action dated Oct. 8, 2020.

Ceunen et al. "Steviol Glycosides: Chemical Diversity, Metabolism, and Function," J. Nat. Prod. 2013, 76, 1201-1228 (Year: 2013); Cited in Non-Final Office Action dated Oct. 8, 2020.

Brown et al. "Non-Nutritive Sweeteners and their Role in the Gastrointestinal Tract," J Clin Endocrinol Metab. Aug. 2012; 97(8): 2597-2605 (Year: 2012); Cited in Non-Final Office Action dated Oct. 8, 2020.

Pepino "Metabolic effects of non-nutritive sweeteners," Physiology & Behavior 152 (2015) 450-455 (Year: 2015; Cited in Non-Final Office Action dated Oct. 8, 2020.

Sobolevskaya et al. "Bioactive metabolites of the marine actinobacterium *Streptomyces* sp. KM M 721 0," Russian Chemical Bulletin, International Edition, vol. 56, No. 4, pp. 838-840, Apr. 2007 (Year: 2007); Cited in Non-Final Office Action dated Oct. 8, 2020.

Gondry et al. "Cyclodipeptide synthases are a family of tRNA-dependent peptide bond-forming enzymes," Nature Chemical Biology, 2009, 5(6):414-20 (Year: 2009) ; Cited in Non-Final Office Action dated Oct. 8, 2020.

Healthline Sucrose vs Glucose vs Fructose: What's the difference? downloaded from www.healthline.com/nutrition/sucrose-glucose-fructose on Oct. 2, 2020 (Year: 2020) ; Cited in Non-Final Office Action dated Oct. 8, 2020.

Drugbank entry for Sweetening Agents, Accessopm No. DBCAT000378 downloaded from go.drugbank.com/categories/ DBCAT000378 on Oct. 3, 2020 (Year: 2020); Cited in Non-Final Office Action dated Oct. 8, 2020.

Non-Final Office Action dated Oct. 8, 2020, issued in counterpart U.S. Appl. No. 15/746,834.

Restriction/Election Requirement dated Jun. 25, 2020, issued in counterpart U.S. Appl. No. 15/746,834.

Prasad et al., "Could Dietary Proteins Serve as Cyclo(His-Pro) Precursors?", Neuropeptides, 1991, pp. 17-21, Longman Group, UK Ltd, UK.

Perrotta, E. et al, "2,6-Diketopeperazines from Amino Acids, from Solution-Phase to Solid-Phase Organic Synthesis", Journal of Combinatorial Chemistry, Jan. 2001, vol. 3, No. 5, pp. 453-460, cited in Extended (supplementary) European Search Report dated Dec. 22, 2016.

Extended (supplementary) European Search Report dated Dec. 22, 2016, issued in counterpart European Application No. 14810329.4. (10 pages).

Prasad et. al., "Could Dietary Proteins Serve as Cyclo(His-Pro) Precursors?", Neuropeptides, Longman Group UK Ltd., 1991, vol. 19, No. 1, pp. 17-21, cited in ISR of PCT/JP2014/065388 (5 pages).

International Search Report dated Sep. 16, 2014, issued in related International Application No. PCT/JP2014/065388 (U.S. Appl. No. 14/896,953, (2 pages).

Kanzaki, H., "Production of novel bioactive compounds by cyclic dipeptide dehydrogenase", Bioscience and Industry, 2002, vol. 60, No. 7, pp. 26-29 (through p. 454-457); with partial English translation; cited in Japanese Office Action dated May 22, 2018.

Office Action dated May 22, 2018, issued in counterpart Japanese Application No. 2015-522799, with English machine translation. (17 pages).

Office Action dated Apr. 6, 2018, issued in counterpart Russian Application No. 2015155291, with English translation. (10 pages).

Search Report dated Apr. 6, 2018, issued in counterpart Russian Application No. 2015155291, with English translation. (5 pages).

Requirement for Restriction Election dated Nov. 20, 2018, issued in U.S. Appl. No. 15/740,060. (11 pages).

Manner et al., "The Antinocicpetive Effects of Branched-Chain Amino Acids:Evidence for Their Ability to Potentiate Morphine Analgesia", Pharmacology Biochemistry and Behavior, 1996, vol. 53, No. 2, pp. 449-454; cited in Requirement for Restriction Election dated Nov. 20, 2018. (6 pages).

Sakurada et al., "Antinociceptive Activities of Synthetic Dipeptides in Mice", J. Pharm. Pharmacol., 1982, 34, pp. 750-751; cited in in Requirement for Restriction Election dated Nov. 20, 2018. (2 pages).

Extended European Search Report dated Jan. 7, 2019, issued in counterpart European U.S. Appl. No. 16818003.2 (5 pages).

Non-Final Office Action dated Feb. 26, 2019, issued in U.S. Appl. No. 15/740,060. (46 pages).

Leucine:the muscle maker, from https://www.wellbeing.com.au/body/fitness/leucine-the-muscle-maker.html, Nov. 9, 2010, pp. 1-2.

High blood pressure, from https://www.mayoclinic.org/diseases-conditions/high-blood-pressure/symptoms-causes/syc . . . , pp. 1-5, accessed Jan. 27, 2019.

Macgill, M., "Everything you need to know about hypertension", from https://www.medicalnewstoday.com/articles/150109.php, Nov. 21, 2018, pp. 1-12.

Causes of Health Failure, from https://www.heart.org/en/health-topics/heart-failure/causes-and-risks-for-heart-failure/causes-of-heart-failure, pp. 1-4, accessed Jan. 27, 2019.

Understanding Heart Failure, from https://my.clevelandclinic.org/health/diseases/17069-heart-failure-understaning-heart-failure, Nov. 9, 2018, pp. 1-10.

Cardiac Disease, from https://www.merckmanuals.com/professional/SearchResults?query=cardiac+disease, pp. 1-18, accessed Jan. 27, 2019.

Giraldo, E. "Overview of Stroke", from https://www.merckmanuals.com/professional/neurologic-disorders/stroke/overview-of-stro . . . , Feb. 2017, pp. 1-9.

Jeppesen, P. B., et al., "Stevioside Acts Directly on Pancreatic beta Cells to Secrete Insulin: Actions Independent of Cyclic Adenosine Monophosphate and Adenosine Triphosphate-Sensitive K+-Channel Activity", Metabolism, Feb. 1, 2000, vol. 49, No. 2, pp. 208-214, XP004631489; cited in EESR dated Apr. 3, 2019.

Herman, L. et al., "Angiotensin Converting Enzyme Inhibitors (ACEI)", from https://www.ncbi.nlm.nih.gov/books/NBK431051/ StatPeals Publishing, Nov. 22, 2018, pp. 1-7.

Extended (supplementary) European Search Report dated Apr. 3, 2019, issued in EP Application No. 16830509.2. (counterpart to U.S. Appl. No. 15/746,834, (9 pages).

Non-Final Office Action dated Sep. 14, 2019, issued in U.S. Appl. No. 14/896,953.

Final Office Action dated Apr. 18, 2019, issued in U.S. Appl. No. 14/896,953.

Prasad, C., "Bioactive Cyclic Dipeptides", Peptides, 1995, vol. 16, No. 1, pp. 151-164; Cited in JP Office Action dated May 22, 2018.

(56) References Cited

OTHER PUBLICATIONS

Ra, K.S. et al., "Hypoglycemic Effects of Cyclo (His-Pro) in Streptozotocin-induced Diabetic Rats", Biotechnology and Bioprocess Engineering, 2012, vol. 17, pp. 176-184; Cited in ISR dated Sep. 20, 2016.
International Search Report dated Sep. 20, 2016, issued in International Application No. PCT/JP2016/071817. (14 pages).
Davis, John S., "The Cyclization of Peptides and Depsipeptides", Journal of Peptide Science, 2003, 9, pp. 471-501; Cited in U.S. Office Action dated Jul. 25, 2019.
Final Office Action dated Jul. 25, 2019, issued in U.S. Appl. No. 15/740,060 (27 pages).
Final Office Action dated Mar. 10, 2021, issued in U.S. Appl. No. 15/746,834 (19 pages).

\* cited by examiner

PLANT EXTRACT CONTAINING DIKETOPIPERAZINE AND METHOD FOR PRODUCING SAME

CROSS-REFERENCE TO RELATED APPLICATIONS

This application is a divisional of U.S. application Ser. No. 14/896,953, filed on Dec. 9, 2015, which is a 371 of International Application No. PCT/JP2014/065388, filed on Jun. 10, 2014, which is based upon and claims the benefit of priority from the prior Japanese Patent Application No. 2013-122259, filed on Jun. 10, 2013, the entire contents of which are incorporated herein by reference.

TECHNICAL FIELD

The present invention relates to a plant extract containing a high concentration of a diketopiperazine and a method for producing the extract.

BACKGROUND ART

"Dipeptides", which are each composed of two amino acids bonded to each other, have been paid attention as functional substances. Dipeptides can be provided with physical properties or novel functions that are not possessed by simple amino acids and are expected as materials having application ranges broader than those of amino acids. In particular, diketopiperazines, which are cyclic dipeptides, are known to have various physiological activities, such as an antibacterial action or an antioxidant action (Non Patent Literatures 1 and 2) and a learning motivation-improving action (Patent Literature 1), and demands for diketopiperazines are predicted to increase in the medical and pharmacological fields.

In general, a diketopiperazine is produced by, for example, chemical synthesis (Non Patent Literature 3) or an enzymatic method (Non Patent Literatures 2 and 4). In addition, a method of synthesizing a cyclic peptide having an arbitrary amino acid sequence by a dehydration and cyclization reactions of a linear peptide in water of high-temperature and high-pressure of a supercritical or subcritical region (Patent Literature 2) and a method of producing a cyclic dipeptide by heat treatment of a linear dipeptide or linear tripeptide in an aqueous solvent (Patent Literatures 3 and 4) have been proposed.

CITATION LIST

Patent Literature

Patent Literature 1: National Publication of International Patent Application No. 2012-517998
Patent Literature 2: Japanese Patent Laid-Open No. 2003-252896
Patent Literature 3: Korean Patent Laid-Open No. 10-2011-0120051
Patent Literature 4: Japanese Patent No. 5456876
Patent Literature 5: Japanese Patent Laid-Open No. 2010-166911
Patent Literature 6: National Publication of International Patent Application No. 2012-517214
Non Patent Literature
Non Patent Literature 1: Peptides, 16(1), 151-164 (1995)
Non Patent Literature 2: Bioscience & Industry, 60(7), 454-457 (2002)
Non Patent Literature 3: J. Comb. Chem., 3, 453-460 (2001)
Non Patent Literature 4: Chemistry Biology, 8, 997-1010 (2001)
Non Patent Literature 5: Agr. Biol. Chem., 38(5), 927-932 (1974)

SUMMARY OF INVENTION

Technical Problem

Although diketopiperazines are thus expected to show various physiological activities in vivo, there are almost no naturally derived diketopiperazines and foods containing high concentrations of diketopiperazines. Naturally derived diketopiperazines are known to be present in fermented foods, such as sherry, Shaoxing wine, soy sauce, sweet cooking rice wine, and vinegar (Non Patent Literature 5), but the contents therein are significantly low. In order to take these foods for obtaining the functionality of the diketopiperazines, considerably large amounts of the foods must be taken. Thus, none of them is practical. Coffee drinks containing Cyclo(Pro-Phe) or Cyclo(Pro-Leu) are also known (Patent Literature 5), but these diketopiperazines are highly bitter and are therefore difficult to be applied to other drinks.

Furthermore, compositions containing relatively large amounts of diketopiperazines derived from animal protein, such as collagen and meat, are known (Patent Literatures 4 and 6). However, because of their flavor, the compositions containing these diketopiperazines derived from animal protein cannot be directly mixed with drinks mainly composed of extracts or juices of plants, such as tea drinks, coffee drinks, soybean drinks, and fruit juice drinks, or soft drinks, such as flavored water, mineral water, and carbonated drinks.

It is an object of the present invention to provide an extract containing a naturally derived and highly safe diketopiperazine at a high concentration and having good flavor and to provide a method for producing the extract.

Solution to Problem

The present inventors, who have diligently studied for solving the above-mentioned problems, have found that a plant extract containing a high concentration of a diketopiperazine can be produced by subjecting a protein-containing plant to decomposition treatment to generate plant peptides and subjecting the plant peptides to high-temperature and high-pressure treatment in a liquid. The inventors have confirmed that this plant extract has a good taste, and have arrived at the completion of the present invention.

The present invention relates to the following aspects:

(1) A plant extract containing at least one of cyclo-alanyl-glutamine, cyclo-alanyl-alanine, cyclo-seryl-tyrosine, cyclo-glycyl-leucine, cyclo-glycyl-tryptophan, cyclo-valyl-valine, cyclo-tryptophanyl-tyrosine, cyclo-leucyl-tryptophan, and cyclo-phenylalanyl-phenylalanine at a concentration of 10 μg/100 g/Bx or more;
(2) The plant extract according to aspect (1), wherein the total amount of diketopiperazine(s) per Bx is 900 μg/100 g/Bx or more;
(3) The plant extract according to aspect (1) or (2), being a tea extract, a soybean extract, or a malt extract;
(4) A plant extract prepared by subjecting a protein-containing plant to decomposition treatment to generate a plant peptide and subjecting the plant peptide to high-temperature and high-pressure treatment in a liquid;

(5) A method for producing a plant extract containing a high concentration of diketopiperazines including cyclo-leucyl-leucine and cyclo-leucyl-phenylalanine, the method comprising a step of subjecting a plant peptide to high-temperature and high-pressure treatment in a liquid;

(6) The method according to aspect (5), wherein the high-temperature and high-pressure treatment is performed in a liquid of 100° C. to 170° C. for from 30 minutes to several hours as heating conditions;

(7) The method according to aspect (5) or (6), wherein the plant peptide is an oligopeptide;

(8) The method according to any one of aspects (5) to (7), wherein the plant peptide is prepared by subjecting a plant-derived protein or a protein-containing plant to decomposition treatment;

(9) The method according to aspect (8), wherein the decomposition treatment is heat treatment or enzyme treatment; and

(10) The method according to aspect (9), wherein the decomposition treatment is enzyme treatment, and the enzyme is an endo-type protease.

Advantageous Effects of Invention

According to the present invention, a plant extract containing a high concentration of a naturally derived and highly safe diketopiperazine can be simply produced in a mass production scale without requiring a troublesome process or complicated facilities.

DESCRIPTION OF EMBODIMENTS (Plant Peptide)

Figure 1:
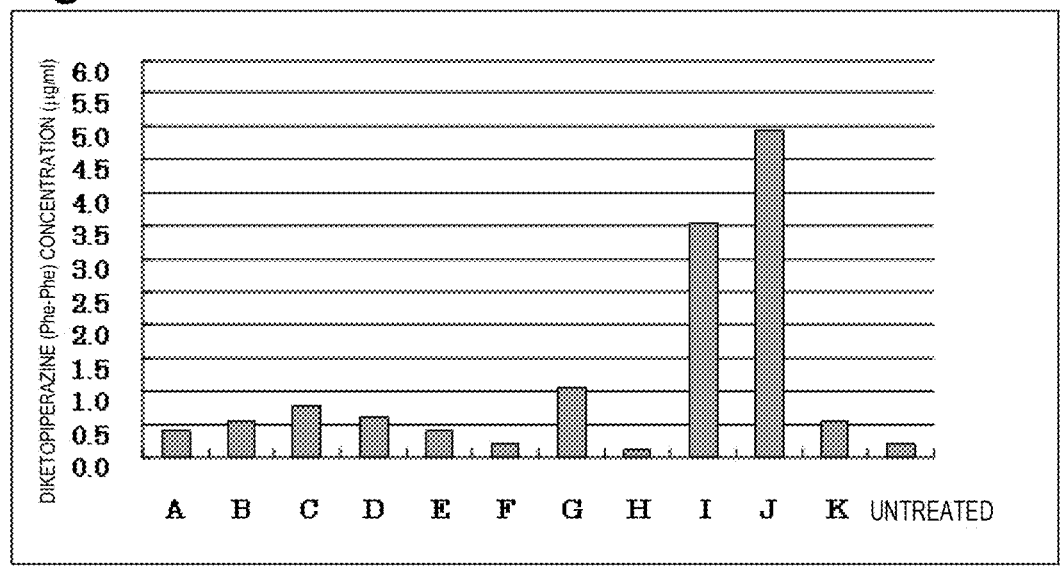
FIG. 1 shows the results of quantitative measurement of cyclo-phenylalanyl-phenylalanine concentration in a plant peptide-processed product prepared from soybean protein.

The plant extract of the present invention can be produced by subjecting plant peptides to high-temperature and high-pressure treatment in a liquid. Herein, the term "plant peptide" refers to a peptide composed of several amino acids linked by depolymerization (oligopeptide formation) of a plant-derived protein or a protein-containing plant through known decomposition treatment (e.g., decomposition treatment with heat or pressure, decomposition treatment with an acid or alkali, or decomposition treatment with an enzyme), unless otherwise specified.

The plant peptide of the present invention can be, for example, a soybean peptide, a barley peptide, a wheat peptide, a wheat germ peptide, a pea peptide, or a rice peptide. As described below, the plant peptide may be prepared from a plant-derived protein or a protein-containing plant or may be a commercial product. Examples of the commercially available plant peptide include soybean peptides, such as HINUTE AM, HINUTE DC, and HINUTE HK (all manufactured by Fuji Oil Co., Ltd.); rice peptides, such as Oryza Peptide P60 (manufactured by Oryza Oil & Fat Chemical Co., Ltd.); wheat peptides, such as Glutamine Peptide GP-1N and Glutamine Peptide GP-N (both manufactured by Nisshin Pharma Inc.); and sesame peptides, such as Sesame Peptide KM-20 (manufactured by KISCO Ltd.).

The examinations by the present inventors demonstrate that the yield of a diketopiperazine mixture varies depending on the sizes of the peptides. The plant peptides preferably include a high proportion of peptides having a molecular weight of 5000 or less, more preferably a molecular weight of 3000 or less, and particularly preferably a molecular weight of 1000 or less. In addition, since the use of soybean having a high amino acid score allows generation of multiple types of diketopiperazines at a high concentration, soybean peptides are one of preferred embodiments.

The plant peptide of the present invention can be a peptide mixture produced using a plant-derived protein or a protein-containing plant as a raw material. Specifically, examples of the peptide mixture include those produced by known decomposition treatment (e.g., decomposition treatment with heat or pressure, decomposition treatment with an acid or alkali, or decomposition treatment with an enzyme) of a raw material: a plant-derived protein, such as soybean protein, wheat protein, wheat germ protein, rice protein, or sesame protein; or an edible protein-containing plant, such as a leaf (e.g., green tea leaves), a seed (e.g., barley, wheat, malt, sesame, or rice), a bean (e.g., soybean, adzuki bean, or black soybean), a potato (e.g., sweet potato or potato). Among these protein-containing plants, soybean, malt, and tea leaves are preferably used in the present invention. In particular, soybean and tea leaves are preferably used, and tea leaves are more preferably used. Decomposition treatment is applied to the above-mentioned plant-derived protein or the protein-containing plant as a raw material to prepare a peptide mixture, which is used as the plant peptide. This decomposition treatment is performed under conditions allowing generation of oligopeptides. Specifically, the decomposition treatment is performed so as to increase the proportion of peptides having a molecular weight of 5000 or less (preferably a molecular weight of 3000 or less and more preferably a molecular weight of 1000 or less).

The decomposition treatment is preferably performed with heat and/or an enzyme because of the easiness (high reaction rate) of generation of an intended oligopeptide and easiness of mass treatment. In particular, decomposition treatment with an enzyme (hereinafter, referred to as enzyme treatment) is preferably employed.

The decomposition treatment by heating is performed in a solvent for preventing the plant or protein from being burned. The amount of the solvent is usually about 10 to 100 parts by mass, preferably about 15 to 80 parts by mass, more preferably about 20 to 60 parts by mass, and particularly preferably about 20 to 40 parts by mass based on 1 part by mass of the plant. The solvent is preferably, for example, water, ethanol, or a mixture thereof and particularly preferably water. The heating may be performed under any conditions that allow generation of peptides. Examples of the heating conditions include heating at 100° C. or more and further at 125° C. or more for 30 minutes to several hours, preferably about 2 to 7 hours. As the heat treatment equipment, for example, a pressure cooker or an autoclave can be used depending on the heating conditions. This heat treatment can be performed simultaneously with the "step of high-temperature and high-pressure treatment in a liquid" of the present invention.

In the production of plant peptides by the enzyme treatment, the enzyme used is a proteolytic enzyme (protease) and is preferably a protease having a high endo-type decomposition activity. The protease is roughly classified into three categories: alkaline protease, neutral protease, and acid protease, based on the difference in optimum pH for the action. In addition, the origin of a protease is a plant origin, an animal origin, or a microbial origin. The enzyme may have any origin and optimum pH that do not cause disadvantageous influences, such as low decomposition efficiency or bad flavor of the resulting decomposition extract.

Examples of the bacterial protease that can be used in the present invention include Protease N, Protease NL, Protease S, and Proleather (R) FG-F (all manufactured by Amano Enzyme Inc.); Protin NY, Protin P, Deskin, Depirays, Protin A, and Thermoase (R) (all manufactured by Daiwa Fine Chemicals Co., Ltd.); Bioplase (R) XL-416F, Bioplase (R) SP-4FG, and Bioplase (R) SP-15FG (all manufactured by Nagase ChemteX Corporation); Orientase (R) 90N, Nucleicin (R), Orientase (R) 10 NL, and Orientase (R) 22BF (all manufactured by HBI Enzymes Inc.); Aloase (R) AP-10 (manufactured by Yakult Pharmaceutical Industry Co., Ltd.); Protamex (R), Neutrase (R), and Alcalase (R) (all manufactured by Novozymes Japan Ltd.); COROLASE N, COROLASE 7089, VERON W, and VERON P (all manufactured by AB Enzymes); Enchiron NBS (manufactured by Rakuto Kasei Industrial Co., Ltd.); and Alkali Protease GL440, Purafect (R) 4000L, Protease 899, and Protex 6L (all manufactured by Genencor Kyowa Co., Ltd.). Examples of aspergillus protease that can be used in the present invention include Protease A, Protease M, Protease P, Umamizyme, Peptidase R, Newlase (R) A, and Newlase (R) F (all manufactured by Amano Enzyme Inc.); Sumizyme (R) AP, Sumizyme (R) LP, Sumizyme (R) MP, Sumizyme (R) FP, and Sumizyme (R) LPL (all manufactured by Shinnihon Chemicals Corporation); Protin (R) FN (manufactured by Daiwa Fine Chemicals Co., Ltd.); Denapsin 2P, Denazyme (R) AP, and XP-415 (all manufactured by Nagase ChemteX Corporation); Orientase (R) 20A, Orientase (R) ONS, and Tetrase (R) S (all manufactured by HBI Enzymes Inc.); Molsin (R) F, PD Enzyme, IP Enzyme, and AO-Protease (all manufactured by Kikkoman Corporation); Sakanase (manufactured by Kaken Pharma Co., Ltd.); Pantidase (R) YP-SS, Pantidase (R) NP-2, and Pantidase (R) P (all manufactured by Yakult Pharmaceutical Industry Co., Ltd.); Flavourzyme (R) (manufactured by Novozymes Japan Ltd.); Kokulase (R) SS and Kokulase (R) P (both manufactured by Mitsui Lifetech Co., Ltd.); and VERON PS and COROLASE PN-L (both manufactured by AB Enzymes). Examples of other proteases that can be used in the present invention include actinomycete proteases (for example, Actinase (R) AS and Actinase (R) AF (both manufactured by Kaken Pharma Co., Ltd.); and Tasinase (R) (manufactured by Genencor Kyowa Co., Ltd.)); plant-derived proteases (for example, Papain W-40 (manufactured by Amano Enzyme Inc.), food-grade purified Papain (manufactured by Nagase ChemteX Corporation)); and animal pepsin and trypsin.

Among the above-mentioned proteases, from the viewpoint of the decomposition efficiency and the flavor of the resulting peptide-containing solution, the protease is preferably a bacterial protease, more preferably a neutral protease derived from *Bacillus subtilis* or a protease derived from *Bacillus amyloliquefaciens* or *Bacillus stearothermophilus*, and particularly preferably a neutral protease derived from *Bacillus subtilis*.

Such a protease is used in an amount within a range of 0.1% to 20% by weight, preferably 1% to 15% by weight, more preferably 3% to 10% by weight, based on the amount of the plant-derived protein or the protein-containing plant. An amount less than the above-mentioned range cannot provide the effect of increasing the yield of peptide generation, whereas an amount higher than the above-mentioned range cannot achieve a considerable increase in the yield of peptide generation, which is disadvantageous in the cost. In the enzyme treatment, water is added to a plant-derived protein or a plant to allow the enzyme to act on the wetted protein or plant. The amount of water to be added is usually about 10 to 50 parts by mass, more preferably about 10 to 30 parts by mass, and particularly preferably about 10 to 20 parts by mass, based on 1 part by mass of the dry protein or plant.

The conditions for the enzyme treatment by a protease may be determined in view of the optimum conditions for the protease and are usually at 20° C. to 70° C. (preferably 30° C. to 60° C. and more preferably 40° C. to 60° C.) for about 30 min to 24 hours (preferably 1 to 12 hours and more preferably 1 to 6 hours).

Since the sites of the actions of enzymes on protein as a substrate are different based on the types of the enzymes, the composition of the diketopiperazine mixture prepared by the present invention can be varied. Accordingly, the enzyme can be selected in view of the composition of a desired diketopiperazine mixture. Two or more enzymes may be used in combination.

When a plant is used as plant peptides, pretreatment for reducing the amount of water-soluble protein contained in the plant is preferably performed before the step of generating peptides by the above-described decomposition treatment. The examinations by the present inventors demonstrate that the reduction in the water-soluble protein in advance considerably increases the yield of peptides generated by decomposition treatment or the yield of diketopiperazines generated by the heat treatment of the present invention. Examples of the pretreatment for removing water-soluble protein include a method in which water-soluble protein is eluted by heating a plant in a liquid, solid-liquid separation is performed to collect the solid (plant), and the solid is decomposed and a method in which a plant is subjected to extraction treatment with an aqueous solvent, such as water, and the extraction residue is then decomposed (hereinafter, these methods are collectively referred to as "pre-extraction"). In the pre-extraction, a plant is immersed in an extracting solvent of which the weight is preferably about 15 times or more, more preferably about 15 to 150 times, the weight of the plant, and the soluble component, such as water-soluble protein, contained in the plant are eluted. In this case, the extracting solvent may be heated in advance. Alternatively, a plant is immersed in an extracting solvent and the solvent may be then heated for extraction. The extracting solvent is preferably pure water and may be pure water appropriately containing an organic solvent, such as ethanol. The extracting solvent may contain minerals for appropriately adjusting the hardness thereof.

The pre-extraction may be performed at any extraction temperature and is usually performed at about 50° C. to 100° C., preferably about 60° C. to 95° C., and more preferably about 70° C. to 90° C. The extraction time is about 1 min to 24 hours, preferably about 3 min to 20 hours. The extraction conditions such as extraction temperature and time are adjusted such that the removal rate of the soluble component in the resulting extraction residue is 60% or more, preferably 70% or more, more preferably 80% or more, more preferably 90% or more, and particularly preferably 95% or more. The removal rate of the soluble component means the relative proportion of the solid collected with the extracting solution when the maximum amount of the removable soluble component is defined as 100%, and is the value calculated by the expression: "(the amount (total amount: g) of solution obtained by pre-extraction×its Brix [Bx])/(the maximum amount (g) of the removable soluble component× its Brix [Bx])×100(%)". Throughout the specification, "the maximum amount of the removable soluble component" is conveniently denoted by "the amount of the solution obtained by repeating, ten times, extraction with boiling water of an amount of 30 times the weight of the plant for 10 min". Throughout the specification, the term "Bx" can be measured with a commercially available Bx scale.

The pre-extraction of a plant may be performed once or several times. The extract obtained by pre-extraction may be discarded or may be used by being added to a food or drink. For example, the extract mixed with a plant extract containing a diketopiperazine prepared by the present invention can be added to a food or drink.

(Heat Treatment)

In the production method of the present invention, diketopiperazines are generated by subjecting such plant peptides to high-temperature and high-pressure treatment in a liquid. The liquid for the high-temperature and high-pressure treatment is preferably pure water and may be pure water appropriately containing an organic solvent, such as ethanol. The extracting solvent may contain minerals for appropriately adjusting the hardness thereof. The liquid for the heat treatment is optionally concentrated or diluted to have a Brix (Bx) of about 0.1 to 50.

Throughout the specification, the term "high-temperature and high-pressure" refers to a temperature of 100° C. or more and a pressure exceeding the atmospheric pressure. As a high-temperature and high-pressure extracting apparatus, for example, a pressure-resistant extracting apparatus, a pressure cooker, or an autoclave can be used depending on the conditions.

The temperature of the high-temperature and high-pressure is preferably 100° C. to 170° C., more preferably 110° C. to 150° C., and particularly preferably 120° C. to 140° C. In the case of using a pressure-resistant extracting apparatus as the heating apparatus, this temperature is the measured outlet temperature of the extraction column. In the case of using an autoclave as the heating apparatus, this temperature is the measured temperature at the center of the pressure vessel. The pressure is preferably 0.101 to 0.79 MPa and more preferably 0.101 to 0.48 MPa. The heating time is preferably about 30 to 500 minutes and more preferably about 60 to 300 minutes.

Further optimum conditions for heat treatment are within a range of time and temperature surrounded by the following coordinate systems (i) to (vi), in which time (min) is plotted on the horizontal axis and temperature (° C.) on the vertical axis.

(i) (170° C., 30 min), (ii) (150° C., 30 min), (iii) (115° C., 180 min), (iv) (105° C., 480 min), (v) (135° C., 480 min), and (vi) (150° C., 180 min).

After the high-temperature and high-pressure treatment in a liquid, the liquid fraction is collected by optionally performing solid-liquid separation to obtain a plant extract containing a high concentration of the diketopiperazines of the present invention. The solid-liquid separation is achieved by filtration and/or centrifugation.

Although the composition of the diketopiperazines in the resulting plant extract containing a high concentration of the diketopiperazines varies depending on the origin (the type of the plant as the raw material) of the plant peptides and the type of the enzyme, the high-temperature and high-pressure treatment of the plant peptides of the present invention in a liquid can increase the amount of at least one diketopiperazine selected from the group consisting of cyclo-alanyl-glutamine (CAS Registry Number: 268221-76-7; Cyclo (Ala-Gln)), cyclo-histidyl-proline (CAS Registry Number: 53109-32-3; Cyclo(His-Pro)), cyclo-alanyl-alanine (CAS Registry Number: 5845-61-4; Cyclo(Ala-Ala)), cyclo-glycyl-proline (CAS Registry Number: 3705-27-9; Cyclo (Gly-Pro)), cyclo-seryl-tyrosine (CAS Registry Number: 21754-31-4; Cyclo(Ser-Tyr)), cyclo-prolyl-threonine (CAS Registry Number: 227777-31-3; Cyclo(Pro-Thr)), cyclo-histidyl-phenylalanine (CAS Registry Number: 56586-95-9; Cyclo(His-Phe)), cyclo-alanyl-proline (CAS Registry Number: 65556-33-4; Cyclo(Ala-Pro)), cyclo-phenylalanyl-serine (CAS Registry Number: 35591-00-5; Cyclo(Phe-Ser)), cyclo-glycyl-leucine (CAS Registry Number: 5845-67-0; Cyclo(Gly-Leu)), cyclo-glycyl-phenylalanine (CAS Registry Number: 10125-07-2; Cyclo(Gly-Phe)), cyclo-propyl-proline (Cyclo(Pro-Pro)), cyclo-glycyl-tryptophan (Cyclo (Gly-Trp)), cyclo-aspartyl-phenylalanine (CAS Registry Number: 5262-10-2; Cyclo(Asp-Phe)), cyclo-valyl-proline (Cyclo(Val-Pro)), cyclo-prolyl-tyrosine (Cyclo(Pro-Tyr)), cyclo-methionyl-proline (Cyclo(Met-Pro)), cyclo-methionyl-methionine (Cyclo(Met-Met)), cyclo-valyl-valine (Cyclo(Val-Val)), cyclo-leucyl-proline (CAS Registry Number: 2873-36-1; Cyclo(Leu-Pro)), cyclo-tryptophanyl-tyrosine (Cyclo(Trp-Tyr)), cyclo-phenylalanyl-proline (CAS Registry Number: 3705-26-8; Cyclo(Phe-Pro)), cyclo-leucyl-tryptophan (CAS Registry Number: 15136-34-2; Cyclo(Leu-Trp)), cyclo-phenylalanyl-tryptophan (CAS Registry Number: 82597-82-8; Cyclo(Phe-Trp)), cyclo-leucyl-phenylalanine (CAS Registry Number: 7280-77-5; Cyclo(Leu-Phe)), cyclo-leucyl-leucine (CAS Registry Number: 952-45-4; Cyclo(Leu-Leu)), and cyclo-phenylalanyl-phenylalanine (CAS Registry Number: 2862-51-3; Cyclo(Phe-Phe)).

In particular, the present invention is advantageous for production of a plant extract containing a high concentration of diketopiperazines including Cyclo(Leu-Leu) and Cyclo (Leu-Phe) in relatively high concentrations. The present invention is also advantageous for production of a plant extract containing a high concentration of Cyclo(Phe-Phe).

A natural plant-derived diketopiperazine containing a high concentration of a specific diketopiperazine can be selectively produced from a plant extract containing a high concentration of the diketopiperazine of the present invention by known purification treatment. Accordingly, from one viewpoint, the present invention relates to a method for producing a plant extract containing a high concentration of diketopiperazines including Cyclo(Leu-Leu) and Cyclo (Phe-Phe), and from another viewpoint, the present invention relates to a method for producing a specific diketopiperazine (for example, Cyclo(Ala-Ala), Cyclo(Leu-Phe), Cyclo(Leu-Leu), or Cyclo(Phe-Phe)).

(Plant Extract)

Throughout the specification, the term "extract" refers to a liquid extract, and a "plant extract" of the present invention refers to a liquid extract prepared by extraction treatment of a plant or its processed product.

The present invention can provide a plant extract containing at least one of Cyclo(Ala-Gln), Cyclo(Ala-Ala), Cyclo(Ser-Tyr), Cyclo(Gly-Trp), Cyclo(Val-Val), Cyclo (Trp-Tyr), Cyclo(Leu-Trp), and Cyclo(Phe-Phe) in an amount per Bx of 10 µg/100 g/Bx or more.

In addition, the present invention can provide a plant extract containing diketopiperazines in a total amount of 900

μg/100 g or more, preferably 1000 μg/100 g or more, more preferably 2000 μg/100 g or more, and particularly preferably 5000 μg/100 g or more. Throughout the specification, unless otherwise specified, the total amount of diketopiperazines refers to the sum of the amounts of Cyclo (Ala-Gln), Cyclo (His-Pro), Cyclo (Ala-Ala), Cyclo (Gly-Pro), Cyclo (Ser-Tyr), Cyclo (Pro-Thr), Cyclo (His-Phe), Cyclo (Ala-Pro), Cyclo (Phe-Ser), Cyclo (Gly-Leu), Cyclo (Gly-Phe), Cyclo (Pro-Pro), Cyclo (Gly-Trp), Cyclo (Asp-Phe), Cyclo (Val-Pro), Cyclo (Pro-Tyr), Cyclo (Met-Pro), Cyclo (Met-Met), Cyclo (Val-Val), Cyclo (Leu-Pro), Cyclo (Trp-Tyr), Cyclo (Phe-Pro), Cyclo (Leu-Trp), Cyclo (Phe-Trp), Cyclo (Leu-Phe), Cyclo (Leu-Leu), and Cyclo (Phe-Phe).

In general, since an extract having a high Bx contains various substances (e.g., bitter substances) derived from the raw material at a high concentration, the extract itself is improper as a drink, and addition of the extract to a drink is also improper due to influence on the flavor or the feeling on the tongue. Accordingly, regarding the addition to drink, a lower Bx is preferred. The present invention can provide a plant extract containing a large amount of diketopiperazines of physiologically active substances and having a low Bx, i.e., a plant extract having a high ratio of the content of diketopiperazines to the Bx. Specifically, provided is a plant extract having a ratio of the total amount (unit: μg/100 g) of the above-mentioned diketopiperazines to Brix (Bx) of 900 (μg/100 g/Bx) or more, preferably 1000 (μg/100 g/Bx) or more, more preferably 2000 (μg/100 g/Bx), and further preferably 5000 (μg/100 g/Bx). The upper limit of the amount of diketopiperazines in an extract is not particularly limited and may be appropriately determined in the light of the solubility of the diketopiperazines and is usually about 1000 mg/100 g or less, preferably about 500 mg/100 g or less, and more preferably about 200 mg/100 g or less.

In the case of a plant extract prepared by applying the production method of the present invention to a plant as a raw material, the generation of by-products is low, because no fermentation is performed. In addition, the pre-extraction reduces the amount of the soluble component to give a plant extract having a characteristic flavor of significantly low bitterness.

Such a plant extract has a good flavor and also an excellent appearance without, for example, precipitation and turbidity and can be therefore used directly as an extract or for seasonings, drinks, and other foodstuffs without performing specific pro-treatment. The plant extract of the present invention contains a large content of diketopiperazines, but has a relative low Bx. Accordingly, the amount to be added to a food or drink (in particular, drink) may be low, which is an advantage of increasing the degree of freedom in design of a food or drink. In particular, the plant extraction can be directly mixed with a drink mainly composed of an extract or juice of a plant, such as a tea drink, a coffee drink, a soybean drink, or a fruit juice drink or a soft drink, such as flavored water, mineral water, or a carbonated drink. For example, a drink mixed with a plant extract of the present invention such that the total amount of diketopiperazines is 10 μg/100 g or more, preferably 20 μg/100 g or more, more preferably 40 μg/100 g or more, and further preferably 60 μg/100 g or more can have good taste without having bitterness.

The plant extract prepared by the present invention may be subjected to, for example, clarification treatment depending on the form of the food or drink to which the plant extract is added. In such a case, the plant extract has an advantage that the clarification can be easily performed, because, for example, that the extract does not contain oil and includes fibers.

Examples of preferred form of the plant extract of the present invention include tea extracts, soybean extracts, and malt extracts. These extracts will now be described in detail.

(Tea Extract)

Throughout the specification, the term "tea extract" refers to a tea extract prepared by extraction treatment of tea leaves. The tea leaves of the extraction raw material are drinkable parts by extraction of a tea plant (scientific name: *Camellia sinensis*), such as leaves and stems of tea leaves. In addition, the tea leaves may be in any form, such as a macrophyll or powder form. The harvest time of tea leaves may be any time and is appropriately selected to obtain a desired flavor.

The plant extract (tea extract) containing a high concentration of diketopiperazines prepared by the present invention is characterized by the production process without performing fermentation to inhibit the generation of by-products and to obtain good flavor. From the viewpoint of this flavor, the tea leaves are preferably of steamed unfermented tea (green tea), such as sencha, bancha, houjicha, gyokuro, kabusecha, and sweet tea, or unfermented kamairi tea, such as ureshinocha, aoyagicha, or a variety of Chinese tea.

The present inventors measured the concentrations of diketopiperazines in tea extracts prepared by extracting commercially available tea leaves. The results demonstrate that fermented tea contains a significantly low amount (about 0 to 200 μg/100 g/Bx) of the diketopiperazines and that green tea does not substantially contain the diketopiperazines (see Table 1, the measurement method is the same as that shown in Example 1).

TABLE 1

| RT (min) | Diketopiperazine concentration (ppm/Bx) | Green tea | Goishicha | Pu-erh tea 1 | Pu-erh tea 2 |
|---|---|---|---|---|---|
| 3.6 | Ala-Gln | 0.0 | 0.0 | 0.0 | 0.0 |
| 3.7 | His-Pro | 0.0 | 0.2 | 0.0 | 0.0 |
| 4.4 | Ala-Ala | 0.0 | 0.0 | 0.0 | 0.0 |
| 5.6 | Gly-Pro | 0.0 | 0.1 | 0.1 | 0.1 |
| 5.8 | Ser-Tyr | 0.0 | 0.0 | 0.0 | 0.0 |
| 5.8 | Pro-Thr | 0.0 | 0.6 | 0.2 | 0.1 |
| 6.5 | His-Phe | 0.0 | 0.0 | 0.0 | 0.0 |
| 6.7 | Ala-Pro | 0.0 | 0.2 | 0.3 | 0.2 |
| 7.4 | Phe-Ser | 0.0 | 0.0 | 0.0 | 0.0 |
| 7.8 | Gly-Leu | 0.0 | 0.0 | 0.0 | 0.0 |
| 8.1 | Gly-Phe | 0.0 | 0.0 | 0.0 | 0.0 |
| 8.6 | Pro-Pro | 0.0 | 0.1 | 0.1 | 0.1 |
| 8.6 | Gly-Trp | 0.0 | 0.0 | 0.0 | 0.0 |
| 8.9 | Asp-Phe | 0.0 | 0.0 | 0.0 | 0.0 |
| 9.2 | Val-Pro | 0.0 | 0.1 | 0.2 | 0.2 |
| 9.4 | Pro-Tyr | 0.0 | 0.1 | 0.1 | 0.1 |
| 9.6 | Met-Pro | 0.0 | 0.0 | 0.0 | 0.0 |
| 10.2 | Met-Met | 0.0 | 0.0 | 0.0 | 0.0 |
| 10.2 | Val-Val | 0.0 | 0.0 | 0.0 | 0.0 |
| 10.7 | Leu-Pro | 0.0 | 0.2 | 0.1 | 0.1 |
| 10.5 | Trp-Tyr | 0.0 | 0.0 | 0.0 | 0.0 |
| 11.0 | Phe-Pro | 0.0 | 0.1 | 0.1 | 0.1 |
| 11.2 | Leu-Trp | 0.0 | 0.0 | 0.0 | 0.0 |
| 11.8 | Phe-Trp | 0.0 | 0.0 | 0.0 | 0.0 |
| 12.3 | Leu-Phe | 0.0 | 0.0 | 0.0 | 0.0 |
| 12.4 | Leu-Leu/Ile-Ile | 0.0 | 0.0 | 0.0 | 0.0 |
| 12.6 | Phe-Phe | 0.0 | 0.0 | 0.0 | 0.0 |
| | Total concentration (ppm/Bx) | 0.0 | 1.9 | 1.2 | 0.8 |
| | Total concentration per unit Bx (μg/100 g/Bx) | 0 | 193 | 119 | 82 |

In contrast, the tea extract of the present invention contains at least one of Cyclo(Ala-Gln), Cyclo(Ala-Ala), Cyclo (Ser-Tyr), Cyclo(Gly-Trp), Cyclo(Val-Val), Cyclo(Trp-Tyr), Cyclo(Leu-Trp), and Cyclo(Phe-Phe) of diketopiperazines, which are not contained in conventional teas, at a concentration of 10 μg/100 g/Bx or more.

Alternatively, the tea extract of the present invention contains each of Cyclo (Ala-Gln), Cyclo (His-Pro), Cyclo (Ala-Ala), Cyclo (Gly-Pro), Cyclo (Ser-Tyr), Cyclo (Pro-Thr), Cyclo (His-Phe), Cyclo (Ala-Pro), Cyclo (Phe-Ser), Cyclo (Gly-Leu), Cyclo (Gly-Phe), Cyclo (Pro-Pro), Cyclo (Asp-Phe), Cyclo (Val-Pro), Cyclo (Pro-Tyr), Cyclo (Met-Pro), Cyclo (Leu-Pro), Cyclo (Phe-Pro), Cyclo (Leu-Phe), and Cyclo (Leu-Leu) at a concentration of 0.1 ppm/Bx (10 μg/100 g/Bx) or more. The tea extract preferably contains each of the above-mentioned diketopiperazines at a concentration of 0.2 ppm/Bx or more, more preferably 0.3 ppm/Bx or more, further preferably 0.4 ppm/Bx or more, and particularly preferably 0.5 ppm/Bx or more. Furthermore, the tea extract can contain each of Cyclo(Gly-Trp), Cyclo(Val-Val), Cyclo(Trp-Tyr), Cyclo(Leu-Trp), Cyclo(Phe-Trp), and Cyclo(Phe-Phe) at a concentration of 0.1 ppm/Bx (10 μg/100 g/Bx) or more, preferably 0.2 ppm/Bx or more, and more preferably 0.3 ppm/Bx or more.

Diketopiperazines known to have strong bitterness are Cyclo(Leu-Pro) and Cyclo(Phe-Pro) of the diketopiperazines contained in coffee drinks (see Japanese Patent Laid-Open No. 2010-166911) and Cyclo(Leu-Trp) of a decomposition treatment product of casein (Protein Research Foundation, Peptide Institute, Inc., No. 2, 1974). The tea extract of the present invention contains these diketopiperazines having strong bitterness, but the extract itself does not substantially have bitterness. An aqueous solution containing Cyclo(Leu-Pro), Cyclo(Phe-Pro), and Cyclo(Leu-Trp) at the same concentrations as those of the tea extract have strong bitterness. It is therefore suggested that other diketopiperazines and tea-derived component present in the tea extract additively or synergistically reduce the bitterness of Cyclo(Leu-Pro), Cyclo(Phe-Pro), and Cyclo(Leu-Trp). In particular, a tea extract having a ratio [(B)/(A)] of the total amount (B) of the diketopiperazines having bitterness, Cyclo(Leu-Pro), Cyclo(Phe-Pro), and Cyclo(Leu-Trp), to the total amount (A) of Cyclo(Leu-Leu) and Cyclo(Leu-Phe) of 1.0 or less (preferably 0.8 or less, more preferably 0.6 or less, and particularly preferably 0.4 or less) is a diketopiperazine-containing extract not having any taste such as bitterness and can be directly added to foods and drinks (in particular, drinks).

The total amount of the diketopiperazines per Bx in the tea extract is 900 μg/100 g/Bx or more, preferably 900 to 30000 μg/100 g/Bx, more preferably 2000 to 25000 μg/100 g/Bx, and particularly preferably 5000 to 20000 μg/100 g/Bx. Such a concentration range is advantageous for producing a food or drink provided with the functions (such as physiological activity) of the diketopiperazines.

Such a tea extract can be conveniently produced by decomposing protein in tea leaves to prepare tea peptides and subjecting the tea peptides to high-temperature and high-pressure treatment. Tea leaves abundantly contain protein at about 25% (Food Composition Table, 5th ed.). Accordingly, it can be expected to obtain tea peptides by decomposition treatment of the protein of tea leaves with an enzyme such as a protease, but the action of proteases on tea leaves cannot give a large amount of tea peptides. Since 80% or more of the whole protein in tea leaves are insoluble protein, it is preferable to prepare tea peptides by efficiently acting a proteolytic enzyme on the protein contained in tea leaves. Specifically, water-soluble protein is removed from tea leaves by pre-treatment, and a proteolytic enzyme, such as a protease, is allowed to act on the resulting extraction residue to prepare tea peptides. That is, the tea extract of the present invention containing a high concentration of diketopiperazines can be conveniently produced by efficiently decomposing water-insoluble protein by sequentially performing the following steps:

(a) extracting tea leaves with water and collecting the extraction residue;

(b) acting an endo-type protease on the extraction residue in the presence of water to decompose the tea leaf protein to prepare a solution containing tea peptides;

(c) subjecting the solution containing tea peptides to high-temperature and high-pressure treatment to prepare a reaction solution; and (d) subjecting the reaction solution to solid-liquid separation treatment to collect a solution containing diketopiperazines, or (a) extracting tea leaves with water and collecting the extraction residue;

(b) acting an endo-type protease on the extraction residue in the presence of water to decompose the tea leaf protein to prepare a solution containing tea peptides;

(d') subjecting the solution containing tea peptides to solid-liquid separation treatment to collect a solution containing tea peptides; and (C') subjecting the solution containing tea peptides to high-temperature and high-pressure treatment to prepare a reaction solution containing diketopiperazines.

The conditions for each step are as described above. In the pre-extraction in the step (a), an extraction residue, such as used tea leaves obtained by extraction treatment in, for example, production of tea drinks, can also be used. Conventionally, the water-insoluble tea protein in tea leaves has not been used as a nutrient source. For example, most of more than 22000 tons of extraction residue generated in production of green tea drinks in Japan have been discarded as unused resources, but the above-described method for producing a tea extract is also useful for effective utilization of such used tea leaves that have been conventionally discarded.

This method can produce tea extract containing a high concentration of Cyclo(Leu-Leu), Cyclo(Leu-Phe), and Cyclo(Ala-Ala). Specifically, the extract contains 10% (weight basis) or more of Cyclo(Leu-Leu), 10% or more of Cyclo(Leu-Phe), and 7% or more of Cyclo(Ala-Ala), based on the total amount of the diketopiperazines in the tea extract. When these weight basis contents are expressed by amounts, the tea extract contains each of these diketopiperazines at a concentration of 5.0 ppm/Bx (500 μg/100 g/Bx) or more, preferably 8.0 ppm/Bx or more, and more preferably 10.0 ppm/Bx or more. The upper limit thereof is about 50.0 ppm/Bx or less, preferably about 40.0 ppm/Bx or less, more preferably about 35.0 ppm/Bx or less, and further preferably about 30.0 ppm/Bx or less.

In addition, it was found that the concentrations of Cyclo (Leu-Leu), Cyclo(Leu-Phe), and Cyclo(Phe-Phe) are notably increased by repeating the water extraction (pre-extraction) of tea leaves in the step (a) more than once. Accordingly, this method is also advantageous for production of Cyclo(Phe-Phe). The present inventors confirmed that a tea extract containing 3.0 ppm/Bx or more of Cyclo (Phe-Phe) prepared by this method has a learning motivation-improving action.

Incidentally, a diketopiperazine having a hydrophobic functional group is known to enhance the hydrophobicity, by being circularized, to a level higher than that of the linear peptide. The results of an accelerated preservation test (55° C., 2 weeks) of the above-described tea extract demonstrate that Cyclo(Phe-Phe), which is a component having the highest hydrophobicity, is stably retained. Accordingly, the tea extract of the present invention is also useful as a Cyclo(Phe-Phe)-containing extract. The content of Cyclo (Phe-Phe) in the tea extract is preferably adjusted to 10 μg/100 g/Bx or more, 20 μg/100 g/Bx or more, or 30 μg/100 g/Bx or more.

(Soybean Extract)

Throughout the specification, the term "soybean extract" refers to a solution prepared by adding water to soybean and performing extraction treatment or milling treatment. The soybean (scientific name: Glycine max) as the raw material may be any species and may be produced in any area. Soybean in a stage of processing, such as crushed soybean, can also be used. The soybean extract in this specification encompasses a solution prepared by adding water to a soybean protein decomposition product, as a matter of convenience.

It is said that protein account for about 30% of soybean. Since the soybean protein does not include a large amount of water-insoluble protein, unlike the tea protein, the pre-treatment for removing water-soluble protein is not essential and may be optionally performed. When the pre-treatment for removing water-soluble protein is not performed, a plant extract (soybean extract) containing a high concentration of diketopiperazines can be more conveniently produced by a one-pot reaction.

The present inventors measured the concentrations of diketopiperazines in soybean peptides in view of that commercially available soybean peptides (powder) have been applied with heat about 180° C. to 220° C. during spray drying.

The results demonstrate that a significantly low amount (about 650 μg/100 g/Bx) of diketopiperazines are present in the commercially available soybean peptides (see Table 2).

In contrast, the soybean extract of the present invention contains at least one of Cyclo(Ala-Gln), Cyclo(Ala-Ala), Cyclo(Ser-Tyr), Cyclo(Gly-Trp), Cyclo(Val-Val), Cyclo (Trp-Tyr), Cyclo(Leu-Trp), and Cyclo(Phe-Phe) of diketopiperazines, which are not contained in conventional soybean protein decomposition products (soybean peptides), in an amount per Bx of 10 μg/100 g/Bx or more.

In addition, the soybean extract of the present invention contains each of Cyclo (Ala-Gln), Cyclo (His-Pro), Cyclo (Ala-Ala), Cyclo (Gly-Pro), Cyclo (Ser-Tyr), Cyclo (Pro-Thr), Cyclo (His-Phe), Cyclo (Ala-Pro), Cyclo (Phe-Ser), Cyclo (Gly-Leu), Cyclo (Gly-Phe), Cyclo (Gly-Trp), Cyclo (Asp-Phe), Cyclo (Val-Pro), Cyclo (Pro-Tyr), Cyclo (Met-Pro), Cyclo (Val-Val), Cyclo (Leu-Pro), Cyclo (Trp-Tyr), Cyclo (Phe-Pro), Cyclo (Leu-Trp), Cyclo (Leu-Phe), Cyclo (Leu-Leu) and Cyclo (Phe-Phe) at a concentration of 0.1 ppm/Bx (10 μg/100 g/Bx) or more. The soybean extract preferably contains each of the above-mentioned diketopiperazines at a concentration of 0.5 ppm/Bx or more, more preferably 0.7 ppm/Bx or more, further preferably 0.9 ppm/Bx or more, particularly preferably 1.0 ppm/Bx or more, and particularly preferably 1.2 ppm/Bx or more. Furthermore, the soybean extract can contain each of Cyclo(Pro-Pro) and Cyclo(Phe-Trp) at a concentration of 0.1 ppm/Bx (10 μg/100 g/Bx) or more, preferably 0.2 ppm/Bx or more, and more preferably 0.3 ppm/Bx or more.

This soybean extract (in particular, an extract prepared using soybean or its ground product as a raw material) contains Cyclo(Leu-Pro), Cyclo(Phe-Pro), and Cyclo(Leu-Trp), which are known as diketopiperazines having strong bitterness, but the extract has reduced bitterness. An aqueous solution containing Cyclo(Leu-Pro) and Cyclo(Phe-Pro) at the same concentrations as those of the soybean extract have strong bitterness. It is therefore suggested that other diketopiperazines and soybean-derived component present in the soybean extract additively or synergistically reduce the bitterness of Cyclo(Leu-Pro), Cyclo(Phe-Pro), and Cyclo (Leu-Trp). In particular, a soybean extract having a ratio [(B)/(A)] of the total amount (B) of the diketopiperazines having bitterness, Cyclo(Leu-Pro), Cyclo(Phe-Pro), and Cyclo(Leu-Trp), to the total amount (A) of Cyclo(Leu-Leu) and Cyclo(Leu-Phe) of 1.0 or less (preferably 0.8 or less, more preferably 0.6 or less, and particularly preferably 0.5 or less) is a diketopiperazine-containing extract having significantly reduced bitterness and can be advantageously mixed with foods and drinks (in particular, drinks).

The total amount of the diketopiperazines per Bx in the soybean extract is 900 μg/100 g/Bx or more, preferably 900 to 30000 μg/100 g/Bx, more preferably 2000 to 25000 μg/100 g/Bx, and particularly preferably 5000 to 20000 μg/100 g/Bx. Such a concentration range is advantageous for producing a food or drink provided with the functions (such as physiological activity) of the diketopiperazines.

The soybean extract of the present invention containing a high concentration of diketopiperazines can be produced by sequentially performing the following steps:
 (x) acting an endo-type protease on soybean or a soybean protein decomposition product in the presence of water to prepare a solution containing soybean peptides;
 (y) subjecting the solution containing soybean peptides to high-temperature and high-pressure treatment to prepare a reaction solution; and
 (z) subjecting the reaction solution to solid-liquid separation treatment to collect a solution containing diketopiperazines.

As in production of the tea extract, the order of the steps (y) and (z) may be exchanged. In addition, before the step (x), a step (w) of removing water-soluble protein may be performed. In the case of using soybean peptides including a large amount of di- or tripeptides as a raw material, the step (x) is performed by:
 (x') adding water to soybean peptides including a large amount of di- or tripeptides to prepare a solution containing the soybean peptides.

The conditions of other steps are the same as those described above.

This method can produce a soybean extract containing a high concentration of Cyclo(Leu-Leu), Cyclo(Leu-Phe), Cyclo(Ser-Tyr), and Cyclo (Pro-Thr). Specifically, the extract contains 8% (weight basis) or more of Cyclo(Leu-Leu), 8% or more of Cyclo(Leu-Phe), and 6% or more of Cyclo(Ser-Tyr), based on the total amount of the diketopiperazines in the soybean extract. The soybean extract contains each of these diketopiperazines at a concentration of 5.0 ppm/Bx (500 μg/100 g/Bx) or more, preferably 6.0 ppm/Bx or more, and more preferably 7.0 ppm/Bx or more. In particular, a soybean extract containing each of Cyclo(Leu-Leu) and Cyclo(Leu-Phe) at 10.0 ppm/Bx or more, preferably 12.0 ppm/Bx or more, can be prepared. The upper limit thereof is about 50.0 ppm/Bx or less, preferably about 40.0 ppm/Bx or less, more preferably about 35.0 ppm/Bx or less, and further preferably about 30.0 ppm/Bx or less.

In addition, this method can provide a soybean extract containing 3.0 ppm/Bx or more, preferably 4.0 ppm/Bx or more, of Cyclo(Phe-Phe), which is not included in soybean peptides, and is therefore also advantageous for producing Cyclo(Phe-Phe) (see Examples described below). Incidentally, it has been confirmed that Cyclo(Phe-Phe), which is a highly hydrophobic component, is stably retained in this soybean extract.

(Malt Extract)

Throughout the specification, the term "malt extract" refers to an extract prepared by extraction treatment of malt or its ground product. The soybean malt (malt) as the raw material may be any species and may be produced in any area. In particular, barley malt, which is germinated seeds of barley, is preferably used. It is practical and efficient to use a fraction containing a large amount of protein separated from barley malt by removing the skin. The fraction containing a large amount of protein can be obtained by, for example, gradually scraping the surface of malt to remove the husk and then collecting a fraction containing a large amount of protein, such as the aleurone layer and endosperm, by scraping. Alternatively, as performed for the tea extract, an extraction residue after pre-extraction can be used. Examples of the extraction residue include the malt pomace generated in the production of beer.

A plant extract (malt extract) containing a high concentration of diketopiperazines can be more conveniently produced by a one-pot reaction by using a fraction containing a large amount of protein as a raw material.

The malt extract of the present invention contains at least one of Cyclo(Ala-Gln), Cyclo(Ala-Ala), Cyclo(Ser-Tyr), Cyclo(Gly-Trp), Cyclo(Val-Val), Cyclo(Trp-Tyr), Cyclo(Leu-Trp), and Cyclo(Phe-Phe), which are diketopiperazines that have been conventionally hard to be extracted, at a concentration of 10 µg/100 g/Bx or more.

In addition, the malt extract of the present invention contains each of Cyclo (Ala-Gln), Cyclo (His-Pro), Cyclo (Ala-Ala), Cyclo (Gly-Pro), Cyclo (Ser-Tyr), Cyclo (Pro-Thr), Cyclo (His-Phe), Cyclo (Ala-Pro), Cyclo (Phe-Ser), Cyclo (Gly-Leu), Cyclo (Gly-Phe), Cyclo (Gly-Trp), Cyclo (Asp-Phe), Cyclo (Val-Pro), Cyclo (Pro-Tyr), Cyclo (Met-Pro), Cyclo (Val-Val), Cyclo (Leu-Pro), Cyclo (Trp-Tyr), Cyclo (Phe-Pro), Cyclo (Leu-Trp), Cyclo (Leu-Phe), Cyclo (Leu-Leu) and Cyclo (Phe-Phe) at a concentration of 0.1 ppm/Bx (50 µg/100 g/Bx) or more. The malt extract preferably contains each of the above-mentioned diketopiperazines at a concentration of 0.3 ppm/Bx or more, more preferably 0.4 ppm/Bx or more, further preferably 0.5 ppm/Bx or more, and particularly preferably 0.6 ppm/Bx or more.

This malt extract contains Cyclo(Leu-Pro), Cyclo(Phe-Pro), and Cyclo(Leu-Trp), which are known as diketopiperazines having strong bitterness, but the extract has reduced bitterness. In particular, a malt extract having a ratio [(B)/(A)] of the total amount (B) of the diketopiperazines having bitterness, Cyclo(Leu-Pro), Cyclo(Phe-Pro), and Cyclo (Leu-Trp), to the total amount (A) of Cyclo(Leu-Leu) and Cyclo(Leu-Phe) of 1.0 or less (preferably 0.8 or less) is a diketopiperazine-containing extract having significantly reduced bitterness and can be advantageously mixed with foods and drinks (in particular, drinks).

The total amount of the diketopiperazines per Bx in the malt extract is 900 µg/100 g/Bx or more, preferably 900 to 30000 µg/100 g/Bx, more preferably 2000 to 25000 µg/100 g/Bx, and particularly preferably 5000 to 20000 µg/100 g/Bx. Such a concentration range is advantageous for producing a food or drink provided with the functions (such as physiological activity) of the diketopiperazines.

The malt extract of the present invention containing a high concentration of diketopiperazines can be produced by sequentially performing the following steps:
(x) acting an endo-type protease on malt or a malt protein decomposition product in the presence of water to prepare a solution containing malt peptides;
(y) subjecting the solution containing malt peptides to high-temperature and high-pressure treatment to prepare a reaction solution; and
(z) subjecting the reaction solution to solid-liquid separation treatment to collect a solution containing diketopiperazines.

As in production of the tea extract, the order of the steps (y) and (z) may be exchanged. In addition, before the step (x), a step (w) of removing water-soluble protein may be performed. The conditions of other steps are the same as those described above.

This method can produce a malt extract containing a high concentration of Cyclo(Leu-Leu), Cyclo(Leu-Phe), and Cyclo(Ala-Ala). Specifically, the malt extract contains each of these diketopiperazines at a concentration of 5.0 ppm/Bx (500 µg/100 g/Bx) or more, preferably 6.0 ppm/Bx or more, and more preferably 7.0 ppm/Bx or more. The upper limit thereof is about 50.0 ppm/Bx or less, preferably about 40.0 ppm/Bx or less, more preferably about 30.0 ppm/Bx or less, and further preferably about 20.0 ppm/Bx or less.

In addition, this method can provide a malt extract containing 1.0 ppm/Bx or more, preferably 2.0 ppm/Bx or more, and further preferably 3.0 ppm/Bx or more of Cyclo(Phe-Phe) and is therefore also advantageous for producing Cyclo(Phe-Phe).

EXAMPLES

The present invention will now be described based on Examples, but is not limited to the following Examples. Throughout the specification, unless otherwise specified, the concentrations are weight basis, and the numerical value ranges each include their endpoints.

Example 1

Production of Diketopiperazine from Plant Peptide

Soybean peptides and sesame peptides were used as plant peptides and were subjected to high-temperature and high-pressure treatment in liquids to produce plant extracts containing high concentrations of diketopiperazines. Specifically, 15 mL of distilled water was added to 3 g of soybean peptides (HINUTE AM, manufactured by Fuji Oil Co., Ltd.) or sesame peptides (KM-20, manufactured by KISCO Ltd.), and the mixture was put in an autoclave (manufactured by Tomy Seiko Co., Ltd.) and was subjected to high-temperature and high-pressure treatment at 135° C. and 0.31 MPa for 3 hours. In addition, as a Comparative Example, the same peptides were used to prepare an extract without being subjected to the high-temperature and high-pressure treatment. After the treatment, 10 mL of each solution was diluted 50-fold, subjected to membrane treatment, and then applied to LC-MS/MS to determine the concentration of each diketopiperazine. The details of the analysis conditions were as shown below. In addition, the Brix (Bx) of each plant extract containing a high concentration of diketopiperazines was measured with a digital refractometer RX-5000a (manufactured by ATAGO Co., Ltd.), and the ratio of the total amount (unit: µg/100 g) of diketopiperazines to Brix (Bx) was calculated.

[Formula 1]
(LC-MS/MS Analysis Conditions)
  LC apparatus: SHIMADZU UFLC XR
  Column: Agilent technologies Zorbax SB-AQ 1.8 μm 2.1×150 mm
  Column temperature: 40° C.
  Mobile phase: A: 0.1% formic acid, B: methanol gradient analysis
  Flow rate: feed ratio of 0.2 mL/min
  Injection amount: 2 μL
  Detector: AB Sciex 4000 Q TRAP (R)—Turbo Spray (ESI)—Scheduled multiple reaction monitoring (MRM)
  Nozzle position: top: 4 mm, side: 7 mm
  MRM detection window: 40 sec, Target Scan Time: 0.5 sec
  [Positive mode] analysis at Scheduled MRM
  Ion source condition: CUR 20.0, CAD 6, IS 5500, TEM 700, GS1 70, GS2 70

Table 2 shows the results (throughout the specification, Cyclo(Leu-Leu) denotes the sum of Cyclo(Leu-Leu) and Cyclo(Ile-Ile)). It was demonstrated that plant extracts containing a high concentration of diketopiperazines can be conveniently produced by the high-temperature and high-pressure treatment in a liquid according to the present invention. In addition, it was suggested that it is possible to increase the amount of at least one diketopiperazine selected from the group consisting of Cyclo (Ala-Gln), Cyclo (His-Pro), Cyclo (Ala-Ala), Cyclo (Gly-Pro), Cyclo (Ser-Tyr), Cyclo (Pro-Thr), Cyclo (His-Phe), Cyclo (Ala-Pro), Cyclo (Phe-Ser), Cyclo (Gly-Leu), Cyclo (Gly-Phe), Cyclo (Pro-Pro), Cyclo (Gly-Trp), Cyclo (Asp-Phe), Cyclo (Val-Pro), Cyclo (Pro-Tyr), Cyclo (Met-Pro), Cyclo (Met-Met), Cyclo (Val-Val), Cyclo (Leu-Pro), Cyclo (Trp-Tyr), Cyclo (Phe-Pro), Cyclo (Leu-Trp), Cyclo (Phe-Trp), Cyclo (Leu-Phe), Cyclo (Leu-Leu), and Cyclo (Phe-Phe). In particular, Cyclo (Leu-Leu) and Cyclo(Leu-Phe) were contained at high concentrations. The content of these diketopiperazines was 21.5% in the plant extract containing them at a high concentration.

TABLE 2

| | Diketopiperazine | Soybean peptide | | Sesame peptide |
|---|---|---|---|---|
| RT (min) | concentration (ppm/Bx) | The present invention 1 | Comparative product | The present invention 2 |
| 3.6 | Cyclo (Ala-Gln) | 6.8 | 0.0 | 3.0 |
| 3.7 | Cyclo (His-Pro) | 6.7 | 0.9 | 1.8 |
| 4.4 | Cyclo (Ala-Ala) | 6.1 | 0.0 | 2.8 |
| 5.6 | Cyclo (Gly-Pro) | 5.3 | 0.0 | 0.3 |
| 5.8 | Cyclo (Ser-Tyr) | 11.7 | 0.0 | 1.3 |
| 5.8 | Cyclo (Pro-Thr) | 8.1 | 0.5 | 2.6 |
| 6.5 | Cyclo (His-Phe) | 6.1 | 0.1 | 3.3 |
| 6.7 | Cyclo (Ala-Pro) | 6.9 | 0.8 | 2.1 |
| 7.4 | Cyclo (Phe-Ser) | 4.3 | 0.1 | 1.3 |
| 7.8 | Cyclo (Gly-Leu) | 4.5 | 0.0 | 4.4 |
| 8.1 | Cyclo (Gly-Phe) | 6.1 | 0.1 | 6.7 |
| 8.6 | Cyclo (Pro-Pro) | 0.4 | 0.0 | 0.1 |
| 8.6 | Cyclo (Gly-Trp) | 1.5 | 0.0 | 0.0 |
| 8.9 | Cyclo (Asp-Phe) | 6.6 | 0.2 | 6.8 |
| 9.2 | Cyclo (Val-Pro) | 5.8 | 0.5 | 0.4 |
| 9.4 | Cyclo (Pro-Tyr) | 3.2 | 0.2 | 0.3 |
| 9.6 | Cyclo (Met-Pro) | 2.7 | 0.5 | 0.1 |
| 10.2 | Cyclo (Met-Met)t | 0.2 | 0.1 | 2.0 |
| 10.2 | Cyclo (Val-Val) | 1.7 | 0.0 | 0.4 |
| 10.7 | Cyclo (Leu-Pro) | 6.9 | 1.1 | 1.5 |
| 10.5 | Cyclo (Trp-Tyr) | 1.0 | 0.0 | 0.3 |
| 11.0 | Cyclo (Phe-Pro) | 8.1 | 0.4 | 0.0 |
| 11.2 | Cyclo (Leu-Trp) | 2.7 | 0.0 | 4.2 |
| 11.8 | Cyclo (Phe-Trp) | 0.3 | 0.1 | 3.9 |
| 12.3 | Cyclo (Leu-Phe) | 14.5 | 0.3 | 5.5 |
| 12.4 | Cyclo (Leu-Leu) | 17.9 | 0.4 | 6.8 |
| 12.6 | Cyclo (Phe-Phe) | 4.3 | 0.0 | 2.8 |
| | Total concentration (ppm/Bx) | 150.7 | 6.5 | 64.6 |
| | Total concentration per unit Bx (μg/100 g/Bx) | 15067 | 652 | 6460 |

Example 2

Production of Cyclo(Phe-Phe) from Plant Peptide

The plant peptides used were as follows:
1) soybean peptides "HINUTE AM" (manufactured by Fuji Oil Co., Ltd.): di and tripeptides: 67%, average molecular weight: 500
2) soybean peptides "HINUTE DC" (manufactured by Fuji Oil Co., Ltd.): chain length: 3 to 7, average molecular weight: 1000
3) soybean peptides "HINUTE HK" (manufactured by Fuji Oil Co., Ltd.)
4) rice peptides "Oryza Peptide" (manufactured by Oryza Oil & Fat Chemical Co., Ltd.): tripeptides: 40% to 50%
5) wheat peptides "Glutamine Peptide GP-1N" (manufactured by Nisshin Pharma Inc.): molecular weight: 5000 to 10000
6) wheat peptides "Glutamine Peptide GP-N" (manufactured by Nisshin Pharma Inc.): molecular weight: 5000 to 10000

To 3 g of the peptides of each plant was added 15 mL of distilled water, and the mixture was put in an autoclave (manufactured by Tomy Seiko Co., Ltd.) and was subjected to high-temperature and high-pressure treatment at 132° C. and 0.29 MPa for 2 hours. After the treatment, 10 mL of each solution was subjected to solid-phase extraction with OASIS MAX (manufactured by Waters Corporation). The resulting solid-phase extract was concentrated under reduced pressure and was then dissolved in 100 μL of DMSO. Using 10 μL of the solution, the concentration of cyclo-phenylalanyl-phenylalanine was determined by high-performance liquid chromatography (HPLC).

Table 3 shows the results. The degree of generation of cyclo-phenylalanyl-phenylalanine varied depending on the type of the peptides. Soybean peptides generated a high concentration of cyclo-phenylalanyl-phenylalanine compared to the cases of using rice peptides and wheat peptides. This suggested that it is preferable to use soybean peptides including peptides having a molecular weight of 5000 or less (in particular, a molecular weight of 1000 or less) at a high proportion. Comparison of different soybean peptides suggested that it is preferable to use oligopeptides having a lower molecular weight and containing a large amount of di- and tripeptides as a raw material.

TABLE 3

| Diketopiperazine concentration (μg/ml) | Soybean peptide | | | Rice peptide | Wheat peptide | |
|---|---|---|---|---|---|---|
| | HINUTE AM | HINUTE DC | HINUTE HK | Oryza Peptide | Glutamine Peptide GP-1N | Glutamine Peptide GP-N |
| Phe-Phe | 38.4 | 25.8 | 15.1 | 3.2 | 0.59 | 0.33 |
| Bx | 20.66 | 20.10 | 19.42 | | | |
| Total concentration per unit Bx (μg/100 g/Bx) | 186 | 128 | 78 | | | |

Example 3

Production of Diketopiperazine from Plant-Derived Protein

A plant-derived protein subjected to decomposition treatment with an enzyme was used as the raw material. The plant-derived protein used was soybean protein (Prolina 900 (manufactured by Fuji Oil Co., Ltd.)) and rice protein (Oryza Protin P70 (manufactured by Oryza Oil & Fat Chemical Co., Ltd.)), and 300 mg of each protein was added to 15 mL of distilled water. To each mixture, was added 15 mg of any of enzyme A (ProteAX), enzyme B (Newlase F3G: acid protease (endopeptidase) derived from *Rhizopus niveus*), enzyme C (Papain W-40: protease derived from *Carica papaya*), enzyme D (protease A "Amano" SD: protease derived from *Aspergillus* sp.), enzyme E (protease M "Amano" SD: protease derived from *Aspergillus* sp.), enzyme F (protease P "Amano" 3SD: derived from *Aspergillus* sp.), enzyme G (Promelain F: protease from *Ananas comosus*), enzyme H (Peptidase R), enzyme I (Thermoase PC10F: protease (endopeptidase) derived from *Bacillus stearothermophilus*), enzyme J (Protin SD-NY10: protease derived from *Bacillus* sp.), and enzyme K (Protin SD-AY10: protease derived from *Bacillus* sp.) (all manufactured by Amano Enzyme Inc.), and the resulting mixture was shaken and mixed at 37° C. for 2 hours. This enzyme-treated solution was then subjected to heat treatment without performing solid-liquid separation. The heat treatment was high-temperature and high-pressure treatment at 132° C. for 2 hours in an autoclave (manufactured by Tomy Seiko Co., Ltd.). In addition, the soybean protein and the rice protein not treated with any enzyme were similarly treated. After the treatment, 10 mL of each solution was subjected to solid-phase extraction with OASIS MAX (manufactured by Waters Corporation). The resulting solid-phase extract was concentrated under reduced pressure and was then dissolved in 100 μL of DMSO. Using 10 μL of the solution, the concentration of cyclo-phenylalanyl-phenylalanine was determined by high-performance liquid chromatography (HPLC).

Figure 2:
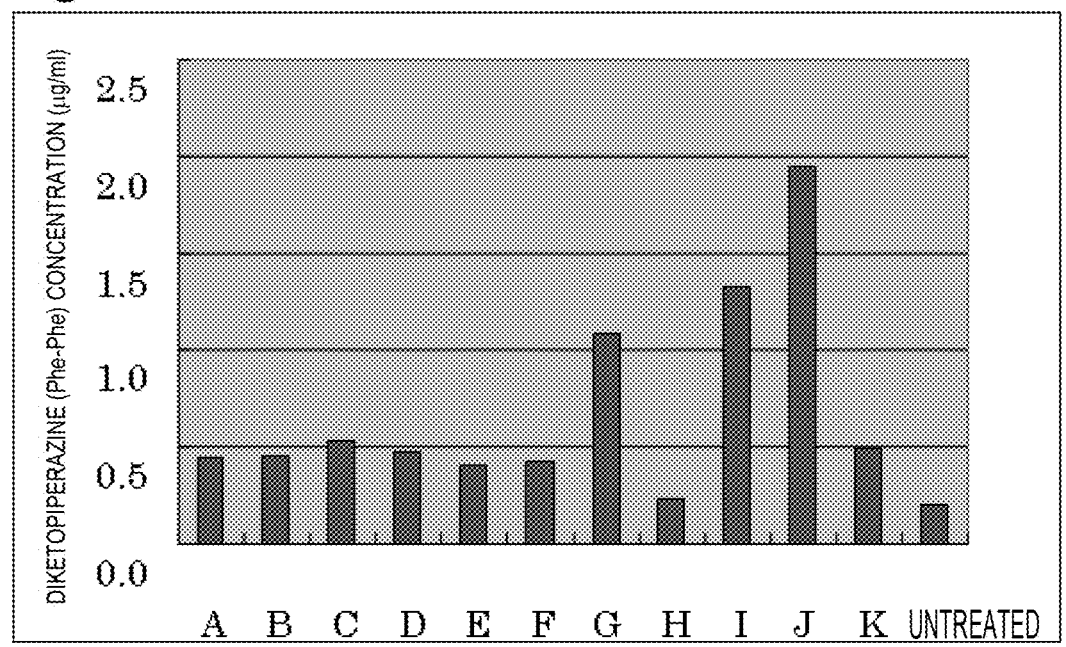
FIG. 2 shows the results of quantitative measurement of cyclo-phenylalanyl-phenylalanine concentration in a plant peptide-processed product prepared from rice protein.

FIG. 1 shows the results in the case of using the soybean protein, and FIG. 2 shows the results in the case of using the rice protein. Protein not subjected to decomposition treatment with an enzyme (Untreated) also generated the diketopiperazine by heat treatment. It was demonstrated that the degree of generation of cyclo-phenylalanyl-phenylalanine varied depending on the type of the enzyme and that there was a tendency that a larger amount of the diketopiperazine was generated by the use of the protease derived from *Bacillus* sp.

Example 4

Production (1) of Diketopiperazine from Plant

As a plant, first-grade tea leaves (species: Yabukita, total nitrogen content: 6.3%) produced in Kagoshima-ken were used. The tea leaves were first subjected to pre-treatment (pre-extraction, three times) for reducing the amount of water-soluble protein. That is, 200 g of boiling water was added to 10 g of the tea leaves, and the mixture was appropriately stirred for 5 min for extraction. After the completion of the extraction, the mixture was filtered through a 140-mesh filter to collect the extraction residue (used tea leaves). To the used tea leaves was poured 200 g of boiling water, and extraction was performed for 5 min. The used tea leaves were collected and were subjected to extraction treatment again, and the used tea leaves were collected.

The tea leaves (used tea leaves) after the pre-extraction were subjected to decomposition treatment with an enzyme. To the used tea leaves (the whole quantity) was poured 200 g of hot water of 50° C., and 1 g of protease (trade name: Protin NY100, manufactured by Daiwa Fine Chemicals Co., Ltd.) was added thereto. The mixture was reacted in a water bath of 55° C. for 3 hours with stirring with a stirring bar (300 rpm) and was then maintained at 95° C. for 30 min to inactivate the enzyme.

This enzyme-treated solution was subjected to heat treatment in the form of a tea leaf-liquid mixture without performing solid-liquid separation. The heat treatment was performed by a high-temperature and high-pressure fluid at 135° C. for 3 hours in an autoclave (manufactured by Tomy Seiko Co., Ltd.). The solution after the treatment was filtered through a 140-mesh filter to obtain a tea extract (extract A). This tea extract (extract A) (Bx: 0.99) was analyzed for the diketopiperazines as in Example 1.

Table 4 shows the results. It was demonstrated that a tea extract including a high concentration of a plant extract containing a high concentration of diketopiperazines can be conveniently produced by subjecting tea leaves (used tea leaves) to high-temperature and high-pressure treatment in a liquid. In addition, it was suggested that it is possible to increase the amount of at least one diketopiperazine selected from the group consisting of Cyclo (Ala-Gln), Cyclo (His-Pro), Cyclo (Ala-Ala), Cyclo (Gly-Pro), Cyclo (Ser-Tyr), Cyclo (Pro-Thr), Cyclo (His-Phe), Cyclo (Ala-Pro), Cyclo (Phe-Ser), Cyclo (Gly-Leu), Cyclo (Gly-Phe), Cyclo (Pro-Pro), Cyclo (Gly-Trp), Cyclo (Asp-Phe), Cyclo (Val-Pro), Cyclo (Pro-Tyr), Cyclo (Met-Pro), Cyclo (Met-Met), Cyclo (Val-Val), Cyclo (Leu-Pro), Cyclo (Trp-Tyr), Cyclo (Phe-Pro), Cyclo (Leu-Trp), Cyclo (Phe-Trp), Cyclo (Leu-Phe), Cyclo (Leu-Leu), and Cyclo (Phe-Phe. In particular, cycloleucyl-leucine and cyclo-leucyl-phenylalanine were contained at high concentrations. The content of these diketopiperazines was 27.2% in the plant extract containing them at a high concentration. In the sensory evaluation of taste, this tea extract was substantially tasteless and odorless.

TABLE 4

| Diketopiperazine concentration (ppm/Bx) | Extract A |
|---|---|
| Cyclo (Ala-Gln) | 6.7 |
| Cyclo (His-Pro) | 3.5 |
| Cyclo (Ala-Ala) | 11.3 |
| Cyclo (Gly-Pro) | 3.3 |
| Cyclo (Ser-Tyr) | 8.9 |
| Cyclo (Pro-Thr) | 6.9 |
| Cyclo (His-Phe) | 4.0 |
| Cyclo (Ala-Pro) | 3.2 |
| Cyclo (Phe-Ser) | 7.1 |
| Cyclo (Gly-Leu) | 9.0 |
| Cyclo (Gly-Phe) | 5.3 |
| Cyclo (Pro-Pro) | 1.7 |
| Cyclo (Gly-Trp) | 2.4 |
| Cyclo (Asp-Phe) | 7.1 |
| Cyclo (Val-Pro) | 2.9 |
| Cyclo (Pro-Tyr) | 1.8 |
| Cyclo (Met-Pro) | 0.9 |
| Cyclo (Met-Met)t | 0.5 |
| Cyclo (Val-Val) | 1.1 |
| Cyclo (Leu-Pro) | 6.8 |
| Cyclo (Trp-Tyr) | 1.3 |
| Cyclo (Phe-Pro) | 1.3 |
| Cyclo (Leu-Trp) | 2.2 |
| Cyclo (Phe-Trp) | 0.8 |
| Cyclo (Leu-Phe) | 17.5 |
| Cyclo (Leu-Leu) | 21.5 |
| Cyclo (Phe-Phe) | 4.2 |
| Total concentration (ppm/Bx) | 143.3 |
| Total concentration per unit Bx (µg/100 g/Bx) | 14326 |

Example 5

Production (2) of Diketopiperazine from Plant

Commercially available soybean boiled in water and malt were used as plants. The soybean boiled in water and malt were each subjected to pre-extraction, three times, with boiling water in an amount of 20 times the dry weight of the plant (soybean), as in Example 4, and were then subjected to enzyme treatment and high-temperature and high-pressure treatment in a liquid, as in Example 3, to prepare a soybean extract (extract B) and a malt extract (extract C). The dry weight of the soybean was assumed as 36.5% of the total amount of the soybean boiled in water, based on the data of the Food Composition Table, 5th ed. The Bx of each of the extract B and the extract C was adjusted to 1, and each extract was then analyzed for the diketopiperazines as in Example 1. Table 5 shows the results. It was demonstrated that plant extracts containing high concentrations of diketopiperazines can also be conveniently produced from soybean and malt.

TABLE 5

| Diketopiperazine concentration (ppm/Bx) | Extract B | Extract C |
|---|---|---|
| Cyclo (Ala-Gln) | 5.0 | 3.2 |
| Cyclo (His-Pro) | 3.2 | 2.0 |
| Cyclo (Ala-Ala) | 6.1 | 8.6 |
| Cyclo (Gly-Pro) | 3.0 | 2.2 |
| Cyclo (Ser-Tyr) | 9.4 | 3.6 |
| Cyclo (Pro-Thr) | 6.8 | 4.0 |
| Cyclo (His-Phe) | 3.7 | 2.2 |
| Cyclo (Ala-Pro) | 1.9 | 2.2 |
| Cyclo (Phe-Ser) | 2.8 | 2.2 |
| Cyclo (Gly-Leu) | 4.5 | 4.1 |
| Cyclo (Gly-Phe) | 5.4 | 2.7 |
| Cyclo (Pro-Pro) | 0.3 | 0.3 |
| Cyclo (Gly-Trp) | 1.1 | 0.6 |
| Cyclo (Asp-Phe) | 8.7 | 4.7 |
| Cyclo (Val-Pro) | 1.2 | 1.7 |
| Cyclo (Pro-Tyr) | 1.3 | 1.4 |
| Cyclo (Met-Pro) | 0.3 | 0.3 |
| Cyclo (Met-Met)t | 0.3 | 0.4 |
| Cyclo (Val-Val) | 1.4 | 0.7 |
| Cyclo (Leu-Pro) | 2.9 | 6.4 |
| Cyclo (Trp-Tyr) | 0.5 | 0.6 |
| Cyclo (Phe-Pro) | 3.3 | 3.3 |
| Cyclo (Leu-Trp) | 2.7 | 1.9 |
| Cyclo (Phe-Trp) | 0.6 | 0.3 |
| Cyclo (Leu-Phe) | 19.6 | 7.7 |
| Cyclo (Leu-Leu) | 24.2 | 9.5 |
| Cyclo (Phe-Phe) | 5.2 | 2.3 |
| Total concentration (ppm/Bx) | 125.5 | 79.4 |
| Total concentration per unit Bx (µg/100 g/Bx) | 12553 | 7936 |

Example 6

Production (3) of Diketopiperazine from Plant

The same tea leaves as those in Example 4 were used as the plant, and the influence of pre-extraction, enzyme treatment, and heat treatment thereon were examined. The samples are shown in Table 6. The samples of sample Nos. 5 and 6 show that the step of generating oligopeptides from a plant and the step of generating dipeptides through cyclization of oligopeptides by high-temperature and high-pressure treatment in a liquid were simultaneously performed by heat treatment. The pre-extraction was performed as in Example 4 except that the number of times was two. The enzyme treatment was performed as in Example 4 except that the reaction temperature was 50° C. The heat treatment was also performed as in Example 4 except that the heating time was changed to 8 hours. The resulting tea extracts (sample Nos. 1 to 8) were analyzed by LC-MS/MS as in Example 1.

TABLE 6

| Sample No. | Pre-extraction | Step (a) | Step (b) |
|---|---|---|---|
| 1 | Not done | Not done | Without heat treatment |
| 2 | Done | | |
| 3 | Not done | With enzyme treatment | |
| 4 | Done | | |
| 5 | Not done | Without enzyme treatment, with heat treatment (135° C., 8 hr) | |
| 6 | Done | | |
| 7 | Not done | With enzyme treatment | With heat treatment (135° C., 8 hr) |
| 8 | Done | | |

Table 7 shows the results. It was revealed that diketopiperazines are not generated if the high-temperature and high-pressure treatment in a liquid is not performed (sample Nos. 1 to 4). In addition, comparison of the samples of sample Nos. 5 to 8 gave the following findings:

The pre-treatment (extraction treatment) increases the diketopiperazine concentration in the resulting tea extract; and Although oligopeptides can be prepared by any of the heat treatment and the enzyme treatment, the enzyme treatment was more effective and efficient.

containing Cyclo(Phe-Phe) at a content per Bx of 10 µg/100 g/Bx or more. Highly hydrophobic Cyclo(Phe-Phe) was stably retained in the extract (in an aqueous solution).

Evaluation of the samples of sample Nos. 5 to 8 for flavor demonstrated that the extracts themselves do not have any taste such as bitterness. Aqueous solutions containing one of or all three of Cyclo(Leu-Pro), Cyclo(Phe-Pro), and Cyclo(Leu-Trp) at the same concentrations as those of the samples of sample No. 5 were prepared and were evaluated for flavor. In these solutions, since bitterness was significantly sensed, it was suggested that the presence of the diketopiperazines in a tea extract reduces bitterness.

TABLE 7

| Diketopiperazine concentration (ppm/Bx) | No. 1 | No. 2 | No. 3 | No. 4 | No. 5 | No. 6 | No. 7 | No. 8 |
| --- | --- | --- | --- | --- | --- | --- | --- | --- |
| Cyclo(Ala-Gln) | 0.0 | 0.0 | 0.0 | 0.0 | 0.2 | 0.3 | 1.9 | 6.6 |
| Cyclo(His-Pro) | 0.0 | 0.0 | 0.0 | 0.0 | 1.1 | 2.7 | 1.3 | 3.4 |
| Cyclo(Ala-Ala) | 0.0 | 0.0 | 0.0 | 0.0 | 0.4 | 1.4 | 5.8 | 11.9 |
| Cyclo(Gly-Pro) | 0.0 | 0.0 | 0.0 | 0.0 | 0.8 | 1.9 | 1.5 | 3.2 |
| Cyclo(Ser-Tyr) | 0.0 | 0.0 | 0.0 | 0.0 | 0.3 | 0.6 | 3.5 | 8.7 |
| Cyclo(Pro-Thr) | 0.0 | 0.0 | 0.0 | 0.0 | 1.3 | 3.1 | 3.2 | 6.9 |
| Cyclo(His-Phe) | 0.0 | 0.0 | 0.0 | 0.0 | 0.2 | 0.4 | 1.3 | 3.9 |
| Cyclo(Ala-Pro) | 0.0 | 0.0 | 0.0 | 0.0 | 0.7 | 2.0 | 1.7 | 3.2 |
| Cyclo(Phe-Ser) | 0.0 | 0.0 | 0.0 | 0.0 | 0.2 | 0.7 | 3.4 | 7.4 |
| Cyclo(Gly-Leu) | 0.0 | 0.0 | 0.0 | 0.0 | 0.2 | 0.6 | 3.9 | 9.6 |
| Cyclo(Gly-Phe) | 0.0 | 0.0 | 0.0 | 0.0 | 0.2 | 0.5 | 1.8 | 5.4 |
| Cyclo(Pro-Pro) | 0.0 | 0.0 | 0.0 | 0.0 | 0.7 | 2.2 | 0.8 | 1.7 |
| Cyclo(Gly-Trp) | 0.0 | 0.0 | 0.0 | 0.0 | 0.0 | 0.1 | 0.6 | 2.4 |
| Cyclo(Asp-Phe) | 0.0 | 0.0 | 0.0 | 0.0 | 0.1 | 0.3 | 1.7 | 6.4 |
| Cyclo(Val-Pro) | 0.0 | 0.0 | 0.0 | 0.0 | 0.5 | 1.5 | 1.3 | 3.0 |
| Cyclo(Pro-Tyr) | 0.0 | 0.0 | 0.0 | 0.0 | 0.3 | 0.9 | 0.8 | 1.8 |
| Cyclo(Met-Pro) | 0.0 | 0.0 | 0.0 | 0.0 | 0.2 | 0.6 | 0.3 | 0.9 |
| Cyclo(Met-Met)t | 0.0 | 0.0 | 0.0 | 0.0 | 0.0 | 0.0 | 0.1 | 0.5 |
| Cyclo(Val-Val) | 0.0 | 0.0 | 0.0 | 0.0 | 0.0 | 0.0 | 0.3 | 1.1 |
| Cyclo(Leu-Pro) | 0.0 | 0.0 | 0.0 | 0.0 | 0.9 | 2.4 | 3.4 | 6.7 |
| Cyclo(Trp-Tyr) | 0.0 | 0.0 | 0.0 | 0.0 | 0.0 | 0.0 | 0.3 | 1.3 |
| Cyclo(Phe-Pro) | 0.0 | 0.0 | 0.0 | 0.0 | 0.1 | 0.9 | 0.6 | 1.3 |
| Cyclo(Leu-Trp) | 0.0 | 0.0 | 0.0 | 0.0 | 0.0 | 0.0 | 0.6 | 2.2 |
| Cyclo(Phe-Trp) | 0.0 | 0.0 | 0.0 | 0.0 | 0.0 | 0.0 | 0.2 | 0.8 |
| Cyclo(Leu-Phe) | 0.0 | 0.0 | 0.0 | 0.0 | 0.1 | 0.4 | 4.1 | 16.5 |
| Cyclo(Leu-Leu) | 0.0 | 0.0 | 0.0 | 0.0 | 0.2 | 0.4 | 6.2 | 20.9 |
| Cyclo(Phe-Phe) | 0.0 | 0.0 | 0.0 | 0.0 | 0.0 | 0.1 | 0.6 | 3.9 |
| Total concentration (ppm/Bx) | 0.0 | 0.0 | 0.0 | 0.0 | 9.1 | 24.0 | 51.1 | 141.6 |
| Total concentration per unit Bx (µg/100 g/Bx) | 0 | 0 | 0 | 0 | 905 | 2402 | 5114 | 14157 |

A plant extract (tea extract) containing a considerably large total amount of diketopiperazines per Bx, such as 900 µg/100 g/Bx or more, was prepared by appropriately performing pre-extraction, heat treatment, and enzyme treatment. This suggests that the present invention is advantageous for a plant extract containing a high concentration of diketopiperazines and production thereof. In addition, it was suggested that a plant extract (tea extract) containing each of Cyclo (Ala-Gln), Cyclo (His-Pro), Cyclo (Ala-Ala), Cyclo (Gly-Pro), Cyclo (Ser-Tyr), Cyclo (Pro-Thr), Cyclo (His-Phe), Cyclo (Ala-Pro), Cyclo (Phe-Ser), Cyclo (Gly-Leu), Cyclo (Gly-Phe), Cyclo (Pro-Pro), Cyclo (Asp-Phe), Cyclo (Val-Pro), Cyclo (Pro-Tyr), Cyclo (Met-Pro), Cyclo (Leu-Pro), Cyclo (Phe-Pro), Cyclo (Leu-Phe), and Cyclo (Leu-Leu) at a concentration of 10 µg/100 g/Bx or more can be prepared. It was suggested that the present invention is also useful for the production of one or more of these diketopiperazines.

Furthermore, Cyclo(Phe-Phe) was generated by performing pre-treatment or enzyme treatment. This suggested that the present invention can provide a plant extract (tea extract)

Example 7

Production (4) of Diketopiperazine from Plant

Since the usefulness of pre-extraction was confirmed in Example 6, the number of times of the pre-extraction was examined. First-grade tea leaves (species: Yabukita, total nitrogen content: 6.3%) produced in Kagoshima-ken were used as the plant. In order to achieve a higher concentration of diketopiperazines, the optimum number of times of pre-extraction was investigated. The pre-extraction was performed by the following procedure. That is, 200 g of boiling water was added to 10 g of tea leaves, and the mixture was appropriately stirred for 5 min for extraction. After the completion of the extraction, the mixture was filtered through a 140-mesh filter, and the extract was discarded. In the level of performing the pre-extraction twice or more, 200 g of boiling water was added again to the used tea leaves collected by filtration, and the same procedure was repeated. To the used tea leaves (initial amount: 10 g) thus subjected to the pre-treatment from zero to three times, 200 g of hot water of 50° C. was poured, and 1 g of an enzyme protease (Amano Enzyme Inc., Protin NY100) was added thereto.

The mixture was reacted in a water bath of 50° C. for 3 hours with stirring with a stirring bar (300 rpm) and was then maintained at 95° C. for 30 min to inactivate the enzyme. The resulting tea leaf-liquid mixture was placed in an autoclave (Tomy Seiko Co., Ltd.) and was subjected to high-temperature and high-pressure treatment at 135° C. for 8 hours, and the resulting solution was filtered through a 140-mesh filter to prepare a tea extract. The Bx of each of the resulting extracts was measured, and the concentration of diketopiperazines was then quantitatively measured by LC-MS/MS as in Example 1.

Figure 3:
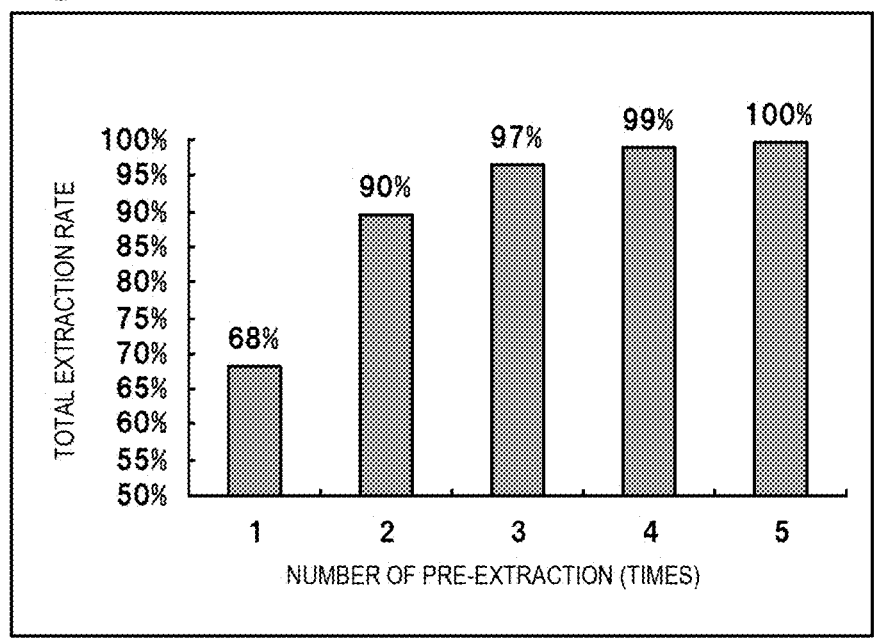
FIG. 3 shows a relationship between the number of times of pre-extraction and the removal rate of the soluble component.

Table 8 shows the results. The amount of generated diketopiperazines increased with the number of times of pre-extraction. FIG. 3 shows a relationship between the number of times of pre-extraction and the removal rate of the soluble component. The removal rate of the soluble component was calculated by the expression: "(the amount (total amount: g) of solution obtained by pre-extraction×its Brix [Bx])/(the amount (g) of solution obtained by repeating ten times the extraction of a plant with boiling water in an amount of 30 times the weight of the plant for 10 min×its Brix [Bx])×100(%)". It was revealed that 95% or more of the soluble component can be removed by repeating pre-extraction three times.

TABLE 8

| Diketopiperazine concentration (ppm/Bx) | The number of times of pre-extraction | | | |
|---|---|---|---|---|
| | zero | once | twice | three times |
| Cyclo (Ala-Gln) | 1.9 | 5.0 | 6.6 | 6.7 |
| Cyclo (His-Pro) | 1.3 | 2.8 | 3.4 | 3.5 |
| Cyclo (Ala-Ala) | 5.8 | 9.6 | 11.9 | 11.3 |
| Cyclo (Gly-Pro) | 1.5 | 2.7 | 3.2 | 3.3 |
| Cyclo (Ser-Tyr) | 3.5 | 7.0 | 8.7 | 8.9 |
| Cyclo (Pro-Thr) | 3.2 | 5.8 | 6.9 | 6.9 |
| Cyclo (His-Phe) | 1.3 | 3.0 | 3.9 | 4.0 |
| Cyclo (Ala-Pro) | 1.7 | 2.7 | 3.2 | 3.2 |
| Cyclo (Phe-Ser) | 3.4 | 6.7 | 7.4 | 7.1 |
| Cyclo (Gly-Leu) | 3.9 | 8.6 | 9.6 | 9.0 |
| Cyclo (Gly-Phe) | 1.8 | 4.5 | 5.4 | 5.3 |
| Cyclo (Pro-Pro) | 0.8 | 1.5 | 1.7 | 1.7 |
| Cyclo (Gly-Trp) | 0.6 | 1.8 | 2.4 | 2.4 |
| Cyclo (Asp-Phe) | 1.7 | 5.2 | 6.4 | 7.1 |
| Cyclo (Val-Pro) | 1.3 | 2.4 | 3.0 | 2.9 |
| Cyclo (Pro-Tyr) | 0.8 | 1.5 | 1.8 | 1.8 |
| Cyclo (Met-Pro) | 0.3 | 0.7 | 0.9 | 0.9 |
| Cyclo (Met-Met)t | 0.1 | 0.0 | 0.5 | 0.5 |
| Cyclo (Val-Val) | 0.3 | 0.8 | 1.1 | 1.1 |
| Cyclo (Leu-Pro) | 3.4 | 6.0 | 6.7 | 6.8 |
| Cyclo (Trp-Tyr) | 0.3 | 0.9 | 1.3 | 1.3 |
| Cyclo (Phe-Pro) | 0.6 | 1.1 | 1.3 | 1.3 |
| Cyclo (Leu-Trp) | 0.6 | 1.7 | 2.2 | 2.2 |
| Cyclo (Phe-Trp) | 0.2 | 0.6 | 0.8 | 0.8 |
| Cyclo (Leu-Phe) | 4.1 | 12.2 | 16.5 | 17.5 |
| Cyclo (Leu-Leu) | 6.2 | 16.9 | 20.9 | 21.5 |
| Cyclo (Phe-Phe) | 0.6 | 2.6 | 3.9 | 4.2 |
| Total concentration (ppm/Bx) | 51.1 | 114.4 | 141.6 | 143.3 |
| Total concentration per unit Bx (µg/100 g/Bx) | 5114 | 11437 | 14157 | 14326 |

Example 8

Production (5) of Diketopiperazine from Plant

Since the usefulness of enzyme treatment was confirmed in Example 6, the type of the enzyme was examined. The enzymes examined were the following nine types:

<Sample No. 9>Protin NY100: protease (endopeptidase) derived from *Bacillus amyloliquefaciens*, <Sample No. 10>Thermoase 160: heat-resistant protease (endopeptidase) derived from *Bacillus stearothermophilus*, <Sample No. 11>Thermoase PC10F: protease (endopeptidase) derived from *Bacillus stearothermophilus*, <Sample No. 12>ProteAX: neutral protease derived from *Aspergillus oryzae*, <Sample No. 13>protease M: neutral protease derived from *Ananas comosus*, <Sample No. 14>protease P: alkaline protease derived from *Aspergillus melleus*, <Sample No. 15>protease A: neutral protease derived from *Aspergillus oryzae*, <Sample No. 16>Peptidase R: neutral protease derived from *Rhizopus oryzae*, and <Sample No. 17>Newlase F3G: acid protease (endopeptidase) derived from *Rhizopus niveus*.

As a plant, first-grade tea leaves (species: Yabukita, total nitrogen content: 6.3%) produced in Kagoshima-ken were used. Each of used tea leaves was prepared from 10 g of the tea leaves by performing pre-extraction three times as in Example 6, 200 g of hot water of 55° C. (70° C. for Thermoase 160 and Thermoase PC10F) was poured thereinto, and 1 g of an enzyme was then added thereto. The mixture was reacted in a water bath of 55° C. (70° C. for Thermoase 160 and Thermoase PC10F) for 3 hours with stirring with a stirring bar (300 rpm) and was then maintained at 95° C. for 30 min to inactivate the enzyme. The resulting tea leaf-liquid mixture was placed in an autoclave (Tomy Seiko Co., Ltd.) and was subjected to high-temperature and high-pressure treatment at 135° C. for 8 hours, and the resulting solution was filtered through a 140-mesh filter to prepare a tea extract. The Bx of each of the resulting extracts was measured, and the concentration of diketopiperazines was then quantitatively measured by LC-MS/MS as in Example 1.

Table 9 shows the results. It was demonstrated that the concentration of diketopiperazines significantly increases by using a bacterial enzyme having a high endopeptidase activity. Among the bacterial enzymes, when neutral protease derived from *Bacillus subtilis* and protease derived from *Bacillus stearothermophilus* were used, the amount of generated diketopiperazines particularly increased.

TABLE 9

| Diketopiperazine concentration (ppm/Bx) | No. 9 | No. 10 | No. 11 | No. 12 | No. 13 | No. 14 | No. 15 | No. 16 | No. 17 |
|---|---|---|---|---|---|---|---|---|---|
| Cyclo(Ala-Gln) | 6.7 | 7.0 | 3.8 | 2.1 | 1.3 | 1.6 | 1.9 | 1.3 | 0.8 |
| Cyclo(His-Pro) | 3.5 | 2.4 | 2.6 | 3.2 | 5.4 | 4.8 | 2.5 | 4.2 | 1.6 |
| Cyclo(Ala-Ala) | 11.3 | 9.8 | 7.5 | 3.8 | 2.3 | 2.7 | 4.1 | 2.1 | 1.4 |

TABLE 9-continued

| Diketopiperazine concentration (ppm/Bx) | No. 9 | No. 10 | No. 11 | No. 12 | No. 13 | No. 14 | No. 15 | No. 16 | No. 17 |
|---|---|---|---|---|---|---|---|---|---|
| Cyclo(Gly-Pro) | 3.3 | 2.2 | 1.9 | 1.2 | 3.5 | 2.6 | 2.4 | 2.8 | 1.6 |
| Cyclo(Ser-Tyr) | 8.9 | 5.7 | 3.5 | 1.6 | 0.7 | 1.3 | 1.2 | 0.8 | 0.4 |
| Cyclo(Pro-Thr) | 6.9 | 5.3 | 3.8 | 4.0 | 7.4 | 6.8 | 5.2 | 6.1 | 3.7 |
| Cyclo(His-Phe) | 4.0 | 4.5 | 3.9 | 0.5 | 0.1 | 0.1 | 0.1 | 0.1 | 0.3 |
| Cyclo(Ala-Pro) | 3.2 | 3.2 | 1.9 | 2.0 | 3.4 | 2.7 | 2.6 | 2.9 | 1.6 |
| Cyclo(Phe-Ser) | 7.1 | 5.3 | 4.9 | 1.5 | 0.8 | 1.2 | 0.9 | 0.9 | 0.7 |
| Cyclo(Gly-Leu) | 9.0 | 19.0 | 10.5 | 1.3 | 1.0 | 1.0 | 1.3 | 0.9 | 0.7 |
| Cyclo(Gly-Phe) | 5.3 | 5.7 | 5.8 | 0.8 | 0.8 | 1.0 | 0.6 | 0.7 | 0.5 |
| Cyclo(Pro-Pro) | 1.7 | 1.9 | 1.4 | 0.7 | 1.8 | 1.9 | 0.6 | 1.7 | 0.8 |
| Cyclo(Gly-Trp) | 2.4 | 2.0 | 0.8 | 0.4 | 0.5 | 0.5 | 0.7 | 0.5 | 0.2 |
| Cyclo(Asp-Phe) | 7.1 | 8.3 | 6.4 | 0.6 | 0.8 | 1.0 | 0.7 | 0.9 | 0.7 |
| Cyclo(Val-Pro) | 2.9 | 1.5 | 1.4 | 2.0 | 3.7 | 3.3 | 2.6 | 3.0 | 1.6 |
| Cyclo(Pro-Tyr) | 1.8 | 1.2 | 1.2 | 1.3 | 3.5 | 2.8 | 2.3 | 2.7 | 1.1 |
| Cyclo(Met-Pro) | 0.9 | 0.5 | 0.5 | 0.7 | 1.4 | 0.8 | 1.3 | 1.0 | 0.0 |
| Cyclo(Met-Met)t | 0.5 | 0.5 | 0.3 | 0.0 | 0.0 | 0.0 | 0.0 | 0.0 | 0.0 |
| Cyclo(Val-Val) | 1.1 | 1.4 | 0.7 | 0.1 | 0.0 | 0.1 | 0.1 | 0.0 | 0.1 |
| Cyclo(Leu-Pro) | 6.8 | 4.5 | 2.5 | 3.1 | 6.9 | 5.5 | 5.4 | 5.1 | 1.9 |
| Cyclo(Trp-Tyr) | 1.3 | 1.5 | 0.6 | 0.1 | 0.0 | 0.1 | 0.1 | 0.1 | 0.0 |
| Cyclo(Phe-Pro) | 1.3 | 1.0 | 0.9 | 1.2 | 3.2 | 2.0 | 2.4 | 2.4 | 0.9 |
| Cyclo(Leu-Trp) | 2.2 | 3.4 | 2.2 | 0.2 | 0.1 | 0.1 | 0.1 | 0.1 | 0.1 |
| Cyclo(Phe-Trp) | 0.8 | 0.9 | 0.5 | 0.0 | 0.0 | 0.0 | 0.0 | 0.0 | 0.0 |
| Cyclo(Leu-Phe) | 17.5 | 4.1 | 10.2 | 1.1 | 0.1 | 0.1 | 0.1 | 0.2 | 0.3 |
| Cyclo(Leu-Leu) | 21.5 | 8.9 | 10.8 | 2.6 | 0.2 | 0.4 | 0.8 | 0.3 | 1.1 |
| Cyclo(Phe-Phe) | 4.2 | 0.8 | 2.5 | 0.0 | 0.0 | 0.0 | 0.0 | 0.0 | 0.1 |
| Total concentration (ppm/Bx) | 143.3 | 112.4 | 92.9 | 36.1 | 49.1 | 44.7 | 40.0 | 40.9 | 21.9 |
| Total concentration per unit Bx (μg/100 g/Bx) | 14326 | 11242 | 9286 | 3607 | 4909 | 4471 | 4001 | 4086 | 2193 |

Example 9

Production (6) of Diketopiperazine from Plant

Tea extracts were produced as in Example 4 except that the concentrations of the enzyme (Protin NY100) were changed to 0% to 20% based on the amount of the tea leaves. The resulting tea extracts were subjected to sensory evaluation, and the contents of 17 types of diketopiperazines shown in Table 10 were measured by LC-MS/MS as in Example 1 and the total amount thereof was determined.

Table 10 shows the results. It was suggested that the enzyme concentration should be within a range of 1% to 20% by weight based on the amount of plant raw material, preferably 3% to 15% by weight and more preferably 4% to 10% by weight. In addition, in all of the tea extracts, since the tea extract itself does not substantially have any taste, these extracts were judged to be extracts that can be used by being added to foods and drinks. In particular, the tea extracts subjected to combinations of pre-extraction, enzyme treatment, and heat treatment had excellent flavor.

TABLE 10

| RT (min) | Diketopiperazine concentration (ppm) | Enzyme concentration | | | | | | | |
|---|---|---|---|---|---|---|---|---|---|
| | | 0.5% | 1% | 2% | 3% | 5% | 10% | 15% | 20% |
| 4.4 | Cyclo(Ala-Gln) | 14.1 | 16.5 | 20.3 | 20.7 | 23.6 | 26.4 | 26.2 | 28.2 |
| 5.6 | Cyclo(His-Pro) | 2.3 | 2.4 | 2.9 | 3.1 | 3.5 | 4.0 | 3.8 | 4.2 |
| 6.7 | Cyclo(Ala-Ala) | 2.0 | 2.2 | 2.6 | 2.7 | 3.1 | 3.5 | 3.5 | 3.7 |
| 7.4 | Cyclo(Gly-Pro) | 5.6 | 5.9 | 7.5 | 7.3 | 8.6 | 9.9 | 10.0 | 10.5 |
| 7.8 | Cyclo(Ser-Tyr) | 10.0 | 11.2 | 13.7 | 13.6 | 14.5 | 15.0 | 13.8 | 13.1 |
| 8.1 | Cyclo(Pro-Thr) | 6.7 | 7.5 | 9.7 | 9.9 | 11.4 | 12.1 | 11.1 | 10.7 |
| 8.6 | Cyclo(His-Phe) | 0.7 | 0.7 | 0.9 | 0.9 | 1.0 | 1.1 | 1.1 | 1.1 |
| 9.2 | Cyclo(Ala-Pro) | 0.7 | 0.7 | 1.0 | 1.0 | 1.3 | 1.6 | 1.7 | 1.9 |
| 9.6 | Cyclo(Phe-Ser) | 0.4 | 0.4 | 0.5 | 0.6 | 0.7 | 0.8 | 0.7 | 0.8 |
| 10.2 | Cyclo(Gly-Leu) | 0.1 | 0.2 | 0.3 | 0.2 | 0.3 | 0.3 | 0.3 | 0.3 |
| 10.2 | Cyclo(Gly-Phe) | 1.0 | 1.3 | 1.7 | 1.7 | 2.0 | 2.2 | 2.2 | 2.2 |
| 10.7 | Cyclo(Pro-Pro) | 1.4 | 1.6 | 2.1 | 2.2 | 2.7 | 3.4 | 3.6 | 4.0 |
| 11 | Cyclo(Gly-Trp) | 1.3 | 1.4 | 1.7 | 1.6 | 1.8 | 2.0 | 2.0 | 2.2 |
| 12.3 | Cyclo(Asp-Phe) | 18.9 | 22.1 | 28.3 | 28.4 | 32.1 | 33.3 | 30.3 | 28.4 |

TABLE 10-continued

| RT (min) | Diketopiperazine concentration (ppm) | Enzyme concentration | | | | | | | |
|---|---|---|---|---|---|---|---|---|---|
| | | 0.5% | 1% | 2% | 3% | 5% | 10% | 15% | 20% |
| 12.4 | Cyclo(Val-Pro) | 11.7 | 12.9 | 15.2 | 14.8 | 16.2 | 15.4 | 13.3 | 12.2 |
| 12.6 | Cyclo(Pro-Tyr) | 2.2 | 2.8 | 4.1 | 4.6 | 5.8 | 7.4 | 7.2 | 7.2 |
| | Total concentration (ppm) | 79.2 | 89.9 | 112.4 | 113.2 | 128.8 | 138.6 | 130.9 | 130.5 |
| | Bx | 0.56 | 0.63 | 0.79 | 0.82 | 0.99 | 1.25 | 1.39 | 1.57 |
| | Total concentration per unit Bx (μg/100 g/Bx) | 14146 | 14267 | 14231 | 13803 | 13010 | 11088 | 9416 | 8310 |

Example 10

Production (7) of Diketopiperazine from Plant

Tea extracts were produced as in Example 4 except that the conditions for the high-temperature and high-pressure treatment were changed. Specifically, the same tea leaves as those in Example 4 were used as the plant at the same amount. Tea leaves (used tea leaves) were prepared by repeating pre-extraction with water three times in an amount of 30 times, instead of 20 times, the amount of the plant and were subjected to enzyme treatment as in Example 4 and to heat treatment with the same heat treatment equipment as that in Example 4 under the various heating conditions shown in Table 11. The resulting tea extracts were analyzed for the diketopiperazines in the extracts as in Example 1.

Table 11 shows the results. It was suggested that generation of diketopiperazines needs heating at 100° C. or more (preferably 115° C. or more and more preferably 125° C. or more) for a heating time of about 30 min to 10 hours and preferably about 2 to 8 hours.

TABLE 11

| Diketopiperazine concentration (ppm/Bx) | Heat treatment condition | | | | |
|---|---|---|---|---|---|
| | 95° C. 30 min | 105° C. 3 h | 115° C. 3 h | 125° C. 3 h | 135° C. 3 h |
| Cyclo (Ala-Gln) | 0.0 | 0.8 | 1.3 | 2.4 | 7.6 |
| Cyclo (His-Pro) | 0.0 | 0.5 | 1.0 | 1.6 | 2.2 |
| Cyclo (Ala-Ala) | 0.0 | 3.2 | 5.8 | 9.7 | 19.8 |
| Cyclo (Gly-Pro) | 0.0 | 0.3 | 0.9 | 1.6 | 3.5 |
| Cyclo (Ser-Tyr) | 0.0 | 0.6 | 1.3 | 3.0 | 5.9 |
| Cyclo (Pro-Thr) | 0.2 | 0.9 | 1.8 | 3.2 | 5.5 |
| Cyclo (His-Phe) | 0.0 | 0.9 | 1.7 | 2.5 | 2.1 |
| Cyclo (Ala-Pro) | 0.0 | 0.8 | 1.2 | 2.0 | 4.9 |
| Cyclo (Phe-Ser) | 0.1 | 1.4 | 1.8 | 2.7 | 6.9 |
| Cyclo (Gly-Leu) | 0.0 | 1.8 | 4.0 | 6.3 | 10.7 |
| Cyclo (Gly-Phe) | 0.1 | 1.7 | 3.1 | 5.7 | 9.2 |
| Cyclo (Pro-Pro) | 0.0 | 0.1 | 0.3 | 0.6 | 1.6 |
| Cyclo (Gly-Trp) | 0.0 | 0.5 | 0.8 | 1.5 | 3.0 |
| Cyclo (Asp-Phe) | 0.2 | 3.1 | 5.3 | 9.4 | 15.5 |
| Cyclo (Val-Pro) | 0.1 | 0.4 | 0.6 | 0.9 | 2.1 |
| Cyclo (Pro-Tyr) | 0.0 | 0.2 | 0.3 | 0.5 | 1.4 |
| Cyclo (Ala-Gln) | 0.0 | 0.0 | 0.1 | 0.3 | 0.7 |
| Cyclo (His-Pro) | 0.0 | 0.2 | 0.3 | 0.4 | 0.8 |
| Cyclo (Ala-Ala) | 0.0 | 0.1 | 0.2 | 0.4 | 1.6 |
| Cyclo (Gly-Pro) | 0.3 | 1.9 | 3.0 | 4.2 | 6.3 |
| Cyclo (Ser-Tyr) | 0.0 | 0.3 | 0.6 | 1.1 | 2.2 |
| Cyclo (Pro-Thr) | 0.0 | 0.0 | 0.3 | 0.7 | 1.4 |
| Cyclo (His-Phe) | 0.0 | 0.5 | 1.2 | 2.4 | 2.7 |
| Cyclo (Ala-Pro) | 0.0 | 0.2 | 0.1 | 0.7 | 1.7 |

TABLE 11-continued

| Diketopiperazine concentration (ppm/Bx) | Heat treatment condition | | | | |
|---|---|---|---|---|---|
| | 95° C. 30 min | 105° C. 3 h | 115° C. 3 h | 125° C. 3 h | 135° C. 3 h |
| Cyclo (Phe-Ser) | 0.1 | 1.9 | 4.7 | 9.7 | 14.4 |
| Cyclo (Gly-Leu) | 0.2 | 2.4 | 5.7 | 12.0 | 17.7 |
| Cyclo (Gly-Phe) | 0.0 | 0.7 | 1.5 | 2.4 | 6.0 |
| Total concentration (ppm/Bx) | 1.3 | 25.5 | 48.9 | 87.8 | 157.5 |
| Total concentration per unit Bx (μg/100 g/Bx) | 130 | 2555 | 4890 | 8781 | 15748 |

Example 11

Production of Diketopiperazine-Containing Food or Drink

Tea extract A produced in Example 4 and/or water in a total amount of 50 g as shown in Table 12 was added to 450 g of a commercially available PET green tea drink to prepare diketopiperazine-containing tea drinks each in the total amount of 500 g. These tea drinks were subjected to sensory evaluation of flavor. The evaluation was performed mainly for bitterness and judged by overall preference based on five criteria: very good flavor (⊚), good flavor (O), drinkable flavor (Δ), flavor slightly difficult to drink (X), and flavor very difficult to drink (XX).

Table 12 shows the results. It was confirmed that all of the tea drinks each in an amount of 500 g including 0 to 50 g of the tea extract A containing the diketopiperazine mixture of Example 4 had good flavor. This suggests that the tea extract prepared by the present invention is a highly versatile material to be mixed in designing the flavor of drinks.

TABLE 12

| | Blending quantity | | | | | |
|---|---|---|---|---|---|---|
| | PET green tea drink (g) | Tea extract (g) | Water (g) | Total amount (g) | Total amount of diketopiperazines (μg/500 g) | Result of sensory evaluation |
| 1 | 450 | 0 | 50 | 500 | 0 | ⊚ |
| 2 | 450 | 5 | 45 | 500 | 57 | ⊚ |
| 3 | 450 | 10 | 40 | 500 | 115 | ⊚ |
| 4 | 450 | 20 | 30 | 500 | 229 | ⊚ |
| 5 | 450 | 30 | 20 | 500 | 344 | ⊚ |
| 6 | 450 | 50 | 0 | 500 | 574 | O |

The invention claimed is:

1. A method for producing a plant extract containing a high concentration of diketopiperazines including cyclo-leucyl-leucine and cyclo-leucyl-phenylalanine, the method comprising a step of subjecting a plant peptide to a treatment at 100° C. to 170° C. and 0.101 to 0.79 Mpa for 30 to 500 minutes in a liquid, wherein the plant peptide is a tea peptide, a soybean peptide, a barley peptide, or a sesame peptide.

2. The method according to claim 1, wherein the treatment is performed in a liquid of 110° C. to 150° C. for from 60 to 500 minutes to.

3. The method according to claim 1, wherein the plant peptide is an oligopeptide.

4. The method according to claim 1, wherein the plant peptide is prepared by subjecting a plant-derived protein or a protein-containing plant to decomposition treatment.

5. The method according to claim 4, wherein the decomposition treatment is heat treatment or enzyme treatment.

6. The method according to claim 5, wherein the decomposition treatment is enzyme treatment, and the enzyme is endo-type protease.

7. The method according to claim 1, wherein the plant extract comprises at least one of cyclo-alanyl-glutamine, cyclo-alanyl-alanine, cyclo-seryl-tyrosine, cyclo-glycyl-leucine, cyclo-glycyl-tryptophan, cyclo-valyl-valine, cyclo-tryptophanyl-tyrosine, cyclo-leucyl-tryptophan, and cyclo-phenylalanyl-phenylalanine at a concentration of 10 μg/100 g/Bx or more.

8. The method according to claim 1, wherein the total amount of diketopiperazine(s) per Bx is 900 μg/100 g/Bx or more.

* * * * *